(12) United States Patent  (10) Patent No.: US 8,409,198 B2
Swanson et al.  (45) Date of Patent: *Apr. 2, 2013

(54) CLAMP BASED METHODS AND APPARATUS FOR FORMING LESIONS IN TISSUE AND CONFIRMING WHETHER A THERAPEUTIC LESION HAS BEEN FORMED

(75) Inventors: David K. Swanson, Campbell, CA (US); Greg Eberl, Sunnyvale, CA (US)

(73) Assignee: ESTECH, Inc. (Endoscopic Technologies, Inc.), San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/214,440

(22) Filed: Aug. 22, 2011

(65) Prior Publication Data

US 2011/0306974 A1   Dec. 15, 2011

Related U.S. Application Data

(63) Continuation of application No. 10/727,144, filed on Dec. 2, 2003, now Pat. No. 8,002,770.

(51) Int. Cl.
 *A61B 18/12* (2006.01)
(52) U.S. Cl. .............................. 606/49; 606/41; 606/52
(58) Field of Classification Search .............. 606/41–52; 607/96, 98, 99, 101, 119
See application file for complete search history.

(56) References Cited

U.S. PATENT DOCUMENTS

| | | | |
|---|---|---|---|
| 463,785 A | 11/1891 | Connable | |
| 1,586,654 A | 6/1926 | Bierman | |
| 2,743,726 A | 5/1956 | Grieshaber | |
| 3,174,309 A | 3/1965 | Kobayashi | |
| 3,316,913 A | 5/1967 | Swenson | |
| 3,503,398 A | 3/1970 | Fogarty et al. | |
| 3,802,437 A | 4/1974 | Kees, Jr. | |
| 3,831,607 A | 8/1974 | Lindemann | |
| 3,920,021 A | 11/1975 | Hiltebrandt | |
| 3,999,555 A | 12/1976 | Person | |
| 4,120,302 A | 10/1978 | Ziegler | |
| 4,201,213 A | 5/1980 | Townsend | |
| 4,306,561 A | 12/1981 | de Medinaceli | |
| 4,469,105 A | 9/1984 | Staver | |
| 4,567,890 A | 2/1986 | Ohta et al. | |
| 4,646,747 A | 3/1987 | Lundback | |
| 4,685,459 A | 8/1987 | Koch et al. | |
| 4,819,633 A | 4/1989 | Bauer et al. | |
| 4,821,719 A | 4/1989 | Fogarty | |
| 4,834,090 A | 5/1989 | Moore | |
| 4,924,864 A | 5/1990 | Danzig | |
| 4,985,030 A | 1/1991 | Melzer et al. | |
| 5,002,561 A | 3/1991 | Fisher | |

(Continued)

FOREIGN PATENT DOCUMENTS

EP   0106748 A1   4/1984
EP   0484671 B1   5/1992

(Continued)

OTHER PUBLICATIONS

International Search Report of PCT/US02/38092 mailed on Mar. 28, 2003, 7 pages.

(Continued)

*Primary Examiner* — Aaron Roane
(74) *Attorney, Agent, or Firm* — Kilpatrick Townsend & Stockton LLP

(57) ABSTRACT

Surgical systems, devices and methods including one or more tissue stimulation elements that, in some instances, may also be used for sensing purposes. Some of the surgical devices also include a tissue coagulation element.

14 Claims, 17 Drawing Sheets

U.S. PATENT DOCUMENTS

| | | | |
|---|---|---|---|
| 5,100,388 A | 3/1992 | Behl et al. |
| 5,131,379 A | 7/1992 | Sewell, Jr. |
| 5,147,357 A | 9/1992 | Rose et al. |
| 5,151,102 A | 9/1992 | Kamiyama et al. |
| 5,190,541 A | 3/1993 | Abele et al. |
| 5,250,072 A | 10/1993 | Jain |
| 5,282,812 A | 2/1994 | Suarez, Jr. |
| 5,290,286 A | 3/1994 | Parins |
| 5,300,065 A | 4/1994 | Anderson |
| 5,300,087 A | 4/1994 | Knoepfler |
| 5,318,564 A | 6/1994 | Eggers |
| 5,324,288 A | 6/1994 | Billings et al. |
| 5,370,650 A | 12/1994 | Tovey et al. |
| 5,398,683 A | 3/1995 | Edwards et al. |
| 5,441,483 A | 8/1995 | Avitall |
| 5,443,463 A | 8/1995 | Stern et al. |
| 5,445,638 A | 8/1995 | Rydell et al. |
| 5,450,846 A | 9/1995 | Goldreyer |
| 5,476,479 A | 12/1995 | Green et al. |
| 5,484,435 A | 1/1996 | Fleenor et al. |
| 5,496,312 A | 3/1996 | Klicek |
| 5,518,164 A | 5/1996 | Hooven |
| 5,540,684 A | 7/1996 | Hassler, Jr. |
| 5,545,193 A | 8/1996 | Fleischman et al. |
| 5,546,682 A | 8/1996 | Skerry |
| 5,569,274 A | 10/1996 | Rapacki et al. |
| 5,571,121 A | 11/1996 | Heifetz |
| 5,575,810 A | 11/1996 | Swanson et al. |
| 5,582,609 A | 12/1996 | Swanson et al. |
| 5,599,350 A | 2/1997 | Schulze et al. |
| 5,624,454 A | 4/1997 | Palti et al. |
| 5,626,607 A | 5/1997 | Malecki et al. |
| 5,637,090 A | 6/1997 | McGee et al. |
| 5,667,517 A | 9/1997 | Hooven |
| 5,673,695 A | 10/1997 | McGee et al. |
| 5,693,051 A | 12/1997 | Schulze et al. |
| 5,707,369 A | 1/1998 | Vaitekunas et al. |
| 5,746,748 A | 5/1998 | Steinberg et al. |
| 5,755,715 A | 5/1998 | Stern et al. |
| 5,755,760 A | 5/1998 | Maguire et al. |
| 5,766,166 A | 6/1998 | Hooven |
| 5,776,130 A | 7/1998 | Buysse et al. |
| 5,782,899 A | 7/1998 | Imran |
| 5,797,905 A | 8/1998 | Fleischman et al. |
| 5,824,005 A | 10/1998 | Motamedi et al. |
| 5,833,690 A | 11/1998 | Yates et al. |
| 5,837,011 A | 11/1998 | Wong |
| 5,843,101 A | 12/1998 | Fry |
| 5,846,239 A | 12/1998 | Swanson et al. |
| 5,888,198 A | 3/1999 | Eggers et al. |
| 5,891,095 A | 4/1999 | Eggers et al. |
| 5,891,140 A | 4/1999 | Ginn et al. |
| 5,908,420 A | 6/1999 | Parins et al. |
| 5,925,038 A | 7/1999 | Panescu et al. |
| 5,938,694 A | 8/1999 | Jaraczewski et al. |
| 5,951,549 A | 9/1999 | Richardson et al. |
| 5,961,513 A | 10/1999 | Swanson et al. |
| 5,971,983 A | 10/1999 | Lesh |
| 5,980,519 A | 11/1999 | Hahnen et al. |
| 6,004,269 A | 12/1999 | Crowley et al. |
| 6,004,320 A | 12/1999 | Casscells et al. |
| 6,010,500 A | 1/2000 | Sherman et al. |
| 6,010,516 A | 1/2000 | Hulka |
| 6,012,457 A | 1/2000 | Lesh |
| 6,022,313 A | 2/2000 | Ginn et al. |
| 6,023,638 A | 2/2000 | Swanson |
| 6,032,674 A | 3/2000 | Eggers et al. |
| 6,039,748 A | 3/2000 | Savage et al. |
| 6,050,996 A | 4/2000 | Schmaltz et al. |
| 6,056,747 A | 5/2000 | Saadat et al. |
| 6,071,279 A | 6/2000 | Whayne et al. |
| 6,076,012 A | 6/2000 | Swanson et al. |
| 6,086,586 A | 7/2000 | Hooven |
| 6,096,033 A | 8/2000 | Tu et al. |
| 6,096,037 A | 8/2000 | Mulier et al. |
| 6,113,596 A | 9/2000 | Hooven et al. |
| 6,115,626 A | 9/2000 | Whayne et al. |
| 6,139,563 A | 10/2000 | Cosgrove, III et al. |
| 6,142,994 A | 11/2000 | Swanson et al. |
| 6,152,920 A | 11/2000 | Thompson et al. |
| 6,161,543 A | 12/2000 | Cox et al. |
| 6,162,220 A | 12/2000 | Nezhat |
| 6,164,283 A | 12/2000 | Lesh |
| 6,174,309 B1 | 1/2001 | Wrublewski et al. |
| 6,179,837 B1 | 1/2001 | Hooven |
| 6,190,381 B1 | 2/2001 | Olsen et al. |
| 6,210,330 B1 | 4/2001 | Tepper |
| 6,228,104 B1 | 5/2001 | Fogarty et al. |
| 6,237,605 B1 | 5/2001 | Vaska et al. |
| 6,245,068 B1 | 6/2001 | Olsen et al. |
| 6,267,761 B1 | 7/2001 | Ryan |
| 6,273,887 B1 | 8/2001 | Yamauchi et al. |
| 6,273,902 B1 | 8/2001 | Fogarty et al. |
| 6,277,117 B1 | 8/2001 | Tetzlaff et al. |
| 6,290,699 B1 | 9/2001 | Hall et al. |
| 6,296,640 B1 | 10/2001 | Wampler et al. |
| 6,308,104 B1 | 10/2001 | Taylor et al. |
| 6,311,692 B1 | 11/2001 | Vaska et al. |
| 6,312,425 B1 | 11/2001 | Simpson et al. |
| 6,312,426 B1 | 11/2001 | Goldberg et al. |
| 6,314,962 B1 | 11/2001 | Vaska et al. |
| 6,314,963 B1 | 11/2001 | Vaska et al. |
| 6,325,797 B1 | 12/2001 | Stewart et al. |
| 6,330,473 B1 | 12/2001 | Swanson et al. |
| 6,334,861 B1 | 1/2002 | Chandler et al. |
| 6,350,264 B1 | 2/2002 | Hooven |
| 6,352,536 B1 | 3/2002 | Buysse et al. |
| 6,387,112 B1 | 5/2002 | Fogarty et al. |
| 6,395,325 B1 | 5/2002 | Hedge et al. |
| 6,416,508 B1 | 7/2002 | Eggers et al. |
| 6,432,103 B1 | 8/2002 | Ellsberry et al. |
| 6,440,130 B1 | 8/2002 | Mulier et al. |
| 6,443,952 B1 | 9/2002 | Mulier et al. |
| 6,454,766 B1 | 9/2002 | Swanson et al. |
| 6,464,699 B1 | 10/2002 | Swanson |
| 6,464,700 B1 | 10/2002 | Koblish et al. |
| 6,468,272 B1 | 10/2002 | Koblish et al. |
| 6,471,699 B1 | 10/2002 | Fleischman et al. |
| 6,511,480 B1 | 1/2003 | Tetzlaff et al. |
| 6,514,250 B1 | 2/2003 | Jahns et al. |
| 6,517,536 B2 | 2/2003 | Hooven et al. |
| 6,522,905 B2 | 2/2003 | Desai |
| 6,522,930 B1 | 2/2003 | Schaer et al. |
| 6,529,756 B1 | 3/2003 | Phan et al. |
| 6,533,784 B2 | 3/2003 | Truckai et al. |
| 6,542,781 B1 | 4/2003 | Koblish et al. |
| 6,544,262 B2 | 4/2003 | Fleischman |
| 6,558,408 B1 | 5/2003 | Fogarty et al. |
| 6,582,429 B2 | 6/2003 | Krishnan et al. |
| 6,584,360 B2 | 6/2003 | Francischelli et al. |
| 6,595,991 B2 | 7/2003 | Tollner et al. |
| 6,610,055 B1 | 8/2003 | Swanson et al. |
| 6,645,202 B1 | 11/2003 | Pless et al. |
| 6,663,622 B1 | 12/2003 | Foley et al. |
| 6,679,882 B1 | 1/2004 | Kornerup |
| 6,685,715 B2 | 2/2004 | Danitz et al. |
| 6,692,491 B1 | 2/2004 | Phan |
| 6,692,514 B2 | 2/2004 | Fogarty et al. |
| 6,706,038 B2 | 3/2004 | Francischelli et al. |
| 6,770,071 B2 | 8/2004 | Woloszko et al. |
| 6,771,996 B2 | 8/2004 | Bowe et al. |
| 6,786,905 B2 | 9/2004 | Swanson et al. |
| 6,807,968 B2 | 10/2004 | Francischelli et al. |
| 6,837,887 B2 | 1/2005 | Woloszko et al. |
| 6,889,694 B2 | 5/2005 | Hooven |
| 6,896,673 B2 | 5/2005 | Hooven |
| 6,899,710 B2 | 5/2005 | Hooven |
| 6,926,712 B2 | 8/2005 | Phan |
| 6,932,812 B2 | 8/2005 | Crowley et al. |
| 6,932,816 B2 | 8/2005 | Phan |
| 6,939,350 B2 | 9/2005 | Phan |
| 6,949,098 B2 | 9/2005 | Mulier et al. |
| 6,997,925 B2 | 2/2006 | Maguire et al. |
| 7,020,531 B1 | 3/2006 | Colliou et al. |
| 7,150,097 B2 | 12/2006 | Sremcich et al. |
| 7,250,048 B2 | 7/2007 | Francischelli et al. |
| 8,002,770 B2 | 8/2011 | Swanson et al. |

| | | | |
|---|---|---|---|
| 2001/0025177 | A1 | 9/2001 | Woloszko et al. |
| 2002/0002372 | A1 | 1/2002 | Jahns et al. |
| 2002/0016588 | A1 | 2/2002 | Wong et al. |
| 2002/0058934 | A1 | 5/2002 | Wang et al. |
| 2002/0099428 | A1 | 7/2002 | Kaufman |
| 2002/0103484 | A1 | 8/2002 | Hooven |
| 2003/0144656 | A1 | 7/2003 | Ocel |
| 2003/0158547 | A1 | 8/2003 | Phan |
| 2003/0158549 | A1 | 8/2003 | Swanson |
| 2004/0059324 | A1 | 3/2004 | Francischelli et al. |
| 2004/0059325 | A1 | 3/2004 | Swanson |
| 2004/0186467 | A1 | 9/2004 | Swanson |
| 2005/0119545 | A1 | 6/2005 | Swanson |
| 2005/0119648 | A1 | 6/2005 | Swanson |
| 2005/0119649 | A1 | 6/2005 | Swanson |
| 2005/0119653 | A1 | 6/2005 | Swanson |
| 2005/0119654 | A1 | 6/2005 | Swanson et al. |
| 2005/0215993 | A1 | 9/2005 | Phan |
| 2006/0155272 | A1 | 7/2006 | Swanson |
| 2006/0155274 | A1 | 7/2006 | Swanson et al. |
| 2006/0195080 | A1 | 8/2006 | Ebert |

FOREIGN PATENT DOCUMENTS

| | | |
|---|---|---|
| EP | 0490301 A1 | 6/1992 |
| EP | 0584787 A1 | 8/1992 |
| EP | 0853922 A1 | 7/1998 |
| EP | 0856291 A2 | 8/1998 |
| EP | 1125549 A2 | 8/2001 |
| JP | 2001515751 A | 9/2001 |
| JP | 2001522622 A | 11/2001 |
| SU | 1253633 A1 | 8/1986 |
| WO | WO 99/12488 A1 | 3/1999 |
| WO | WO 00/24330 A1 | 5/2000 |
| WO | WO 00/42922 A1 | 7/2000 |
| WO | WO 01/72231 A2 | 10/2001 |
| WO | WO 01/80724 A2 | 11/2001 |
| WO | WO 03/070114 A1 | 8/2003 |

OTHER PUBLICATIONS

Written Opinion of PCT/US02/38092 mailed on Nov. 13, 2003, 5 pages.
International Preliminary Examination Report of PCT/US02/38092 mailed on Mar. 12, 2004, 7 pages.
International Search Report of PCT/US02/38105 mailed on Jul. 17, 2003, 5 pages.
Written Opinion of PCT/US02/38105 mailed on Feb. 20, 2004, 5 pages.
International Preliminary Examination Report of PCT/US02/38105 dated May 27, 2004, 5 pages.
International Search Report of PCT/US02/38924 mailed on May 6, 2003, 7 pages.
International Preliminary Examination Report of PCT/US02/38924 dated May 27, 2004, 5 pages.
International Search Report of PCT/US03/29270 mailed on Jan. 12, 2004, 10 pages.
International Search Report of PCT/US2004/039282 mailed on Apr. 7, 2005, 4 pages.
Written Opinion of PCT/US2004/039282 mailed on Apr. 7, 2005, 7 pages.
International Preliminary Report on Patentability of PCT/US2004/039282 dated Jun. 7, 2006, 8 pages.
International Search Report of PCT/US2004/039283 mailed on Apr. 14, 2005, 3 pages.
Written Opinion of PCT/US2004/039283 mailed on Apr. 14, 2005, 7 pages.
International Preliminary Report on Patentability of PCT/US2004/039283 dated Jun. 7, 2006, 8 pages.
International Search Report of PCT/US2004/039284 mailed on May 11, 2005, 3 pages.
Written Opinion of PCT/US2004/039284 mailed on May 11, 2005, 4 pages.
International Preliminary Report on Patentability of PCT/US2004/039284 dated Jun. 7, 2006, 5 pages.
International Search Report of PCT/US2004/039364 mailed on Apr. 12, 2005, 4 pages.
Written Opinion of PCT/US2004/039364 mailed on Apr. 12, 2005, 6 pages.
International Preliminary Report on Patentability of PCT/US2004/039364 dated Jun. 7, 2006, 7 pages.
International Search Report of PCT/US2005/045055 mailed on Oct. 27, 2006, 10 pages.

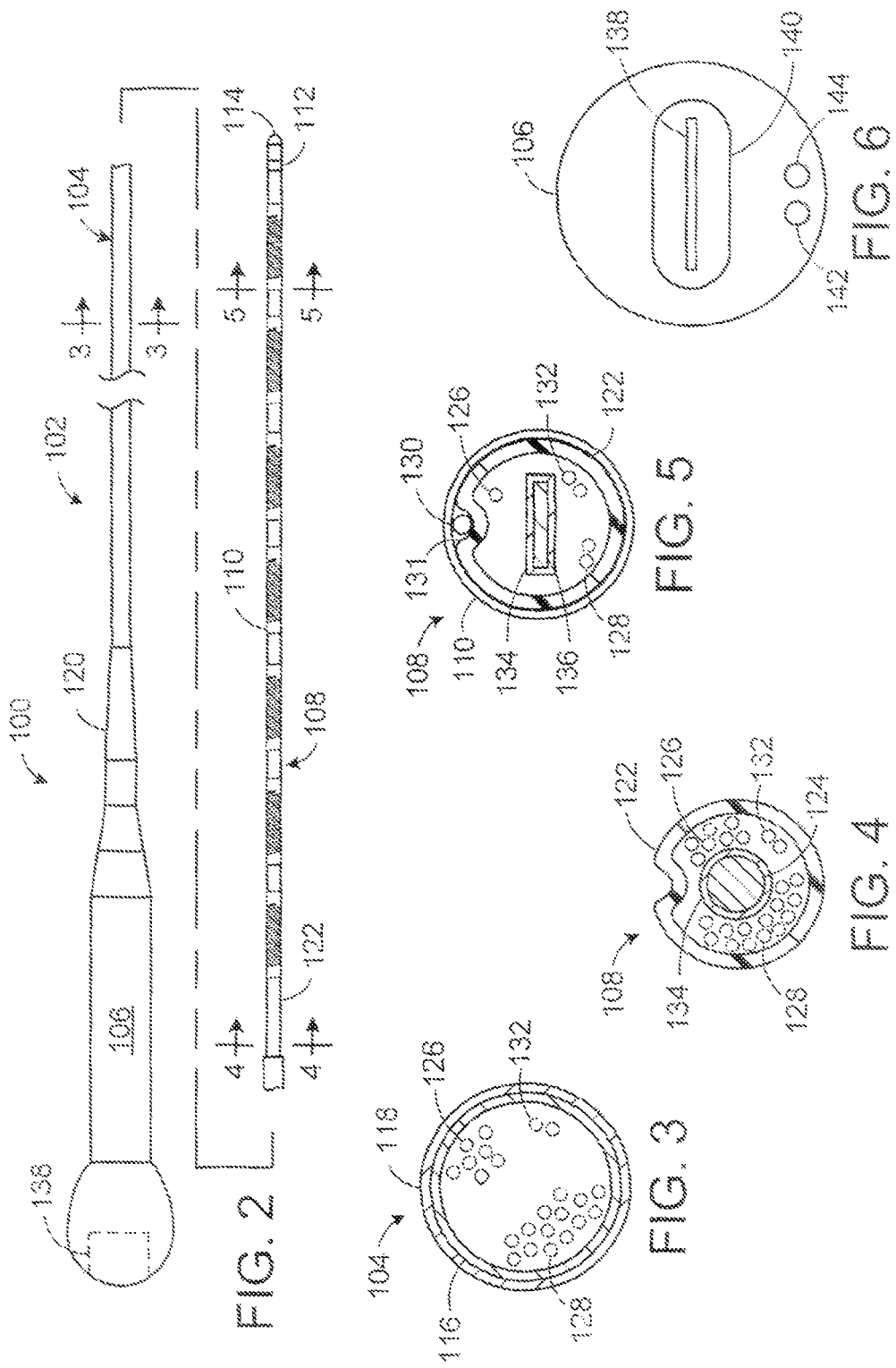

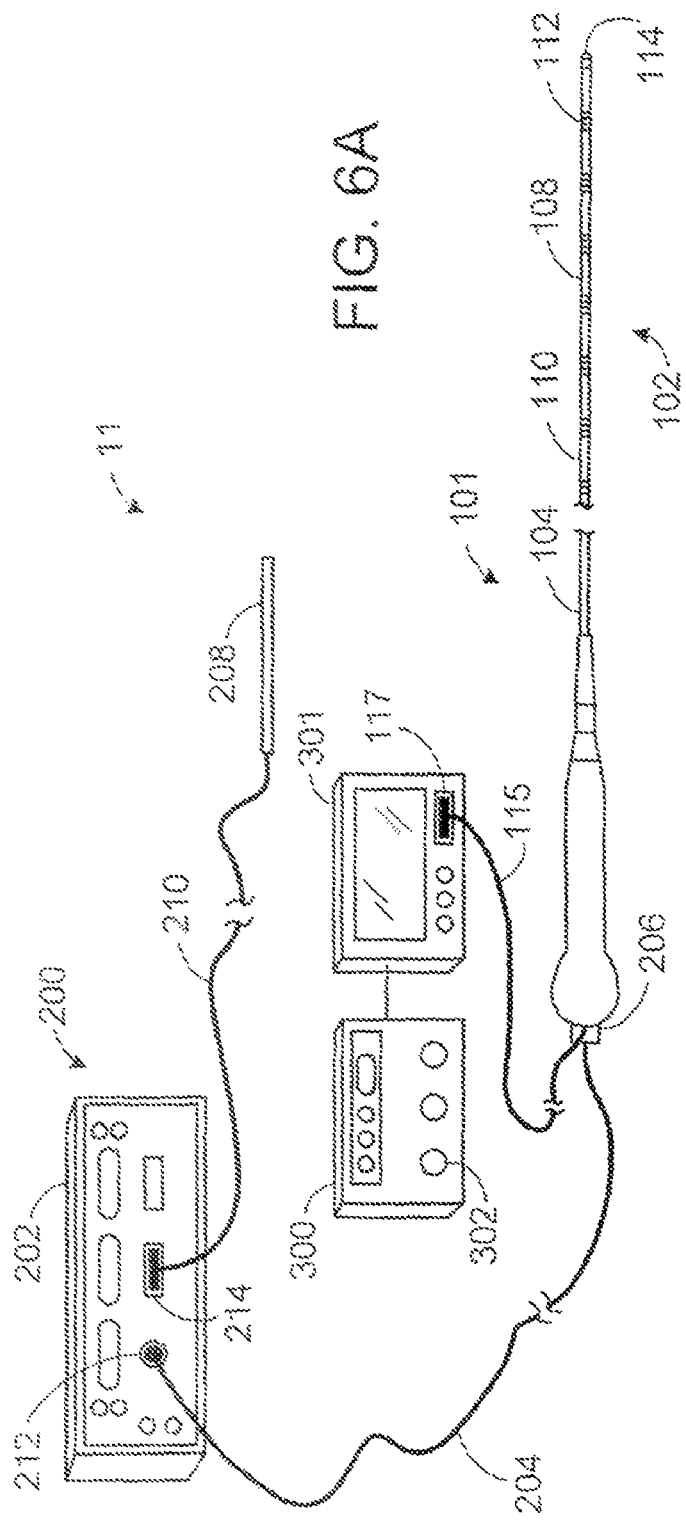
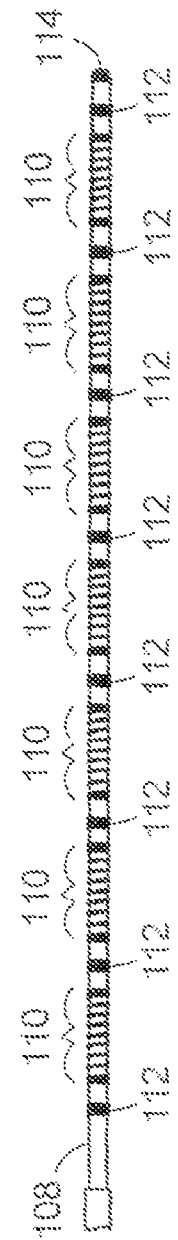
FIG. 6A
FIG. 6B

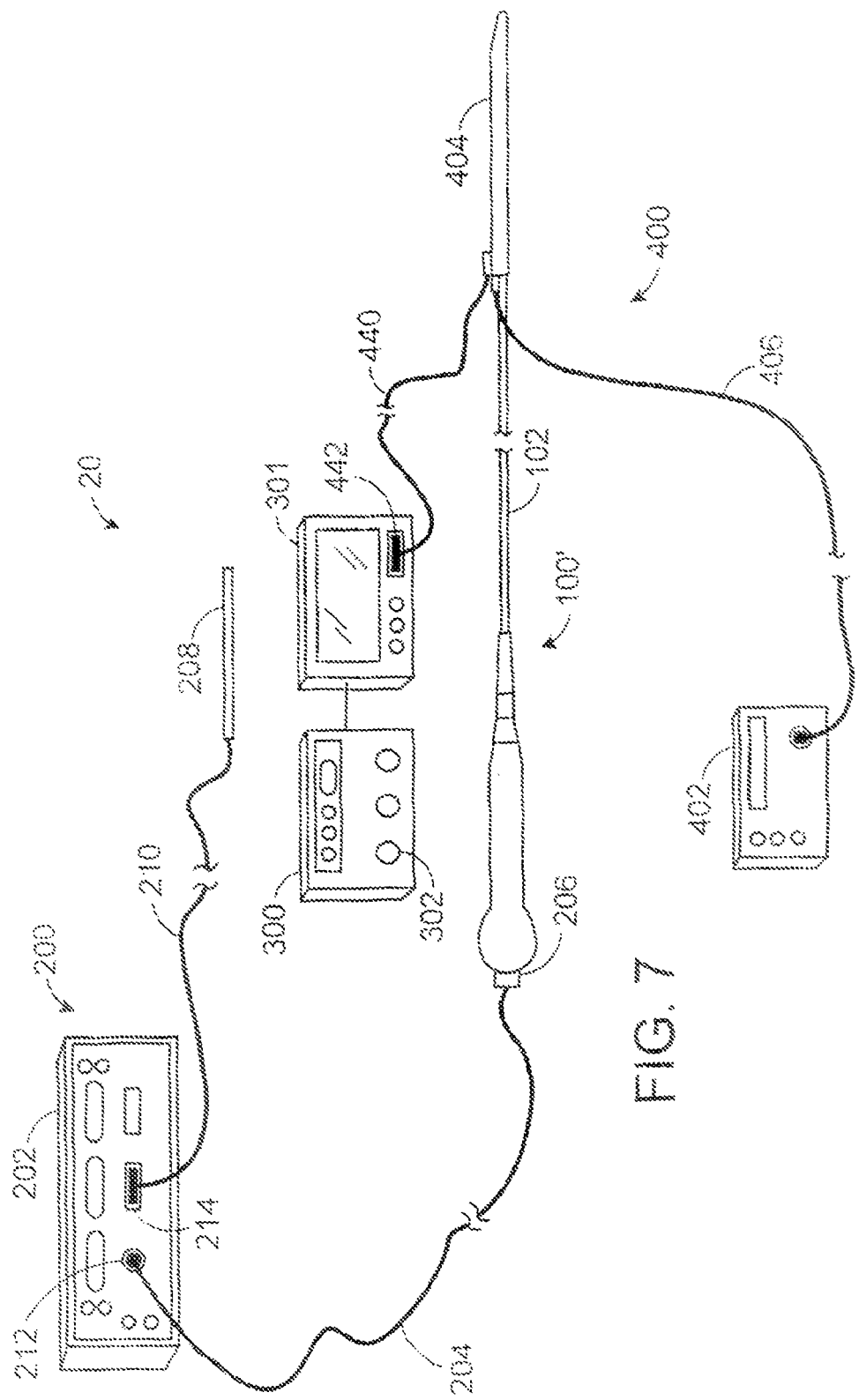

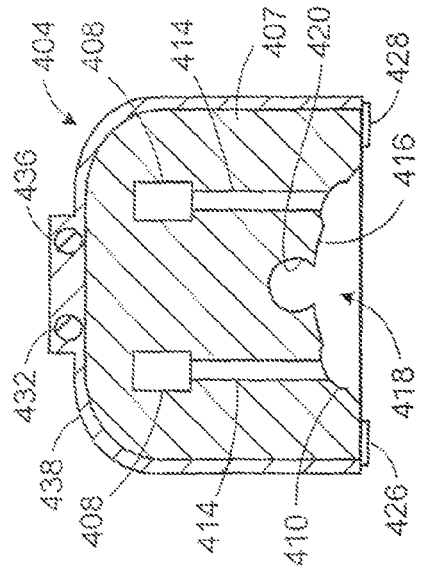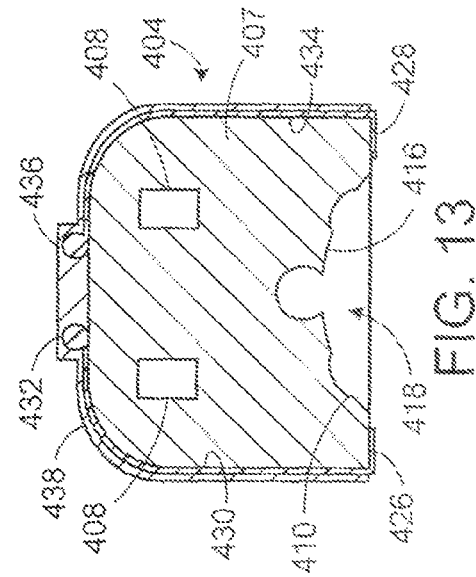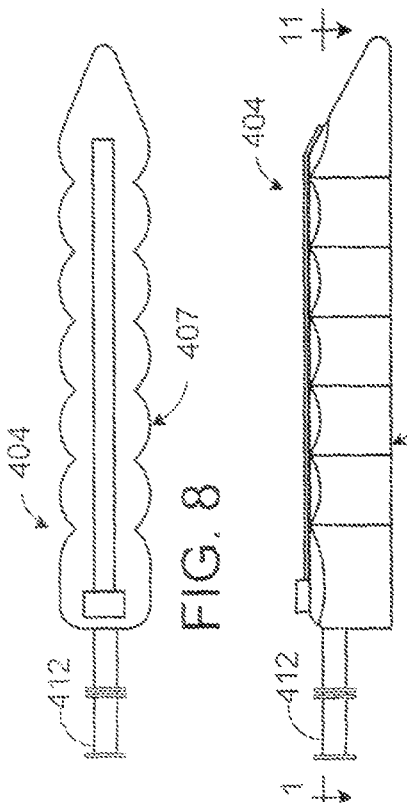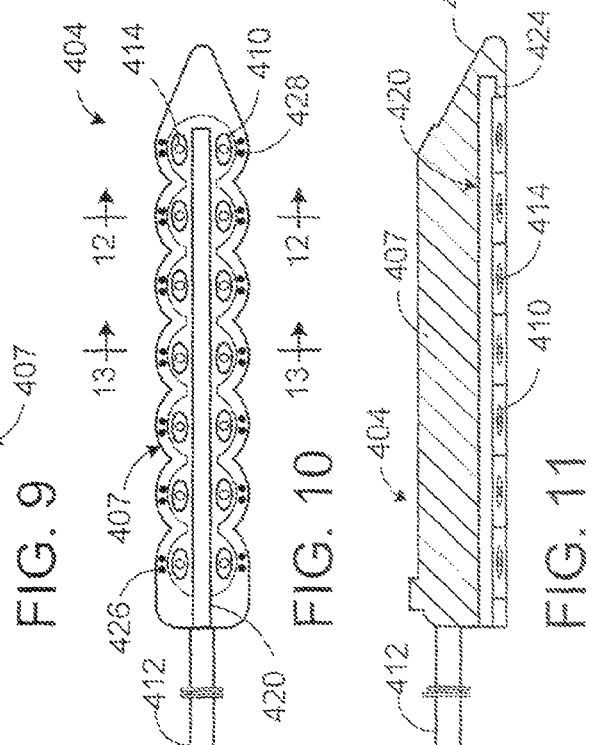

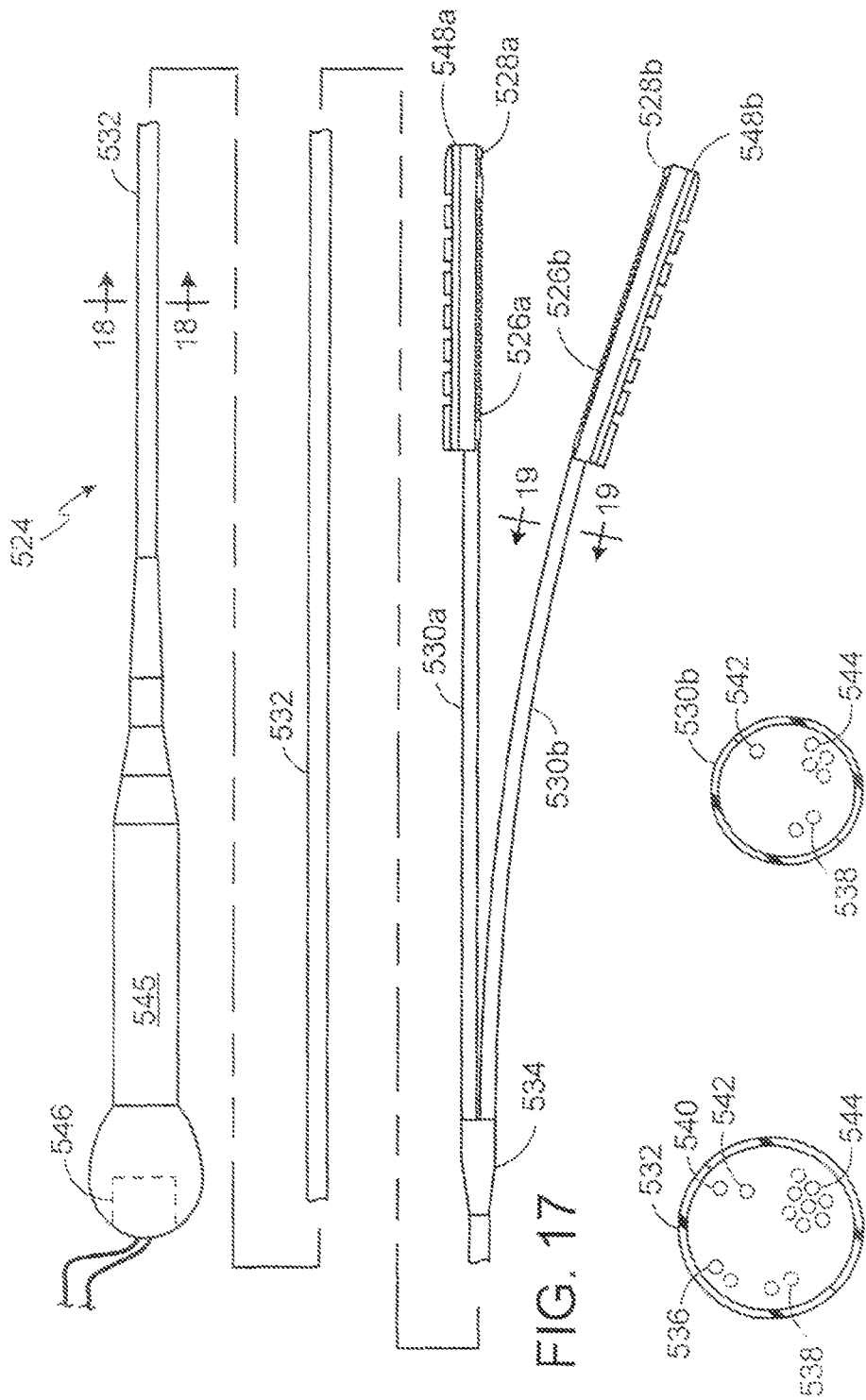

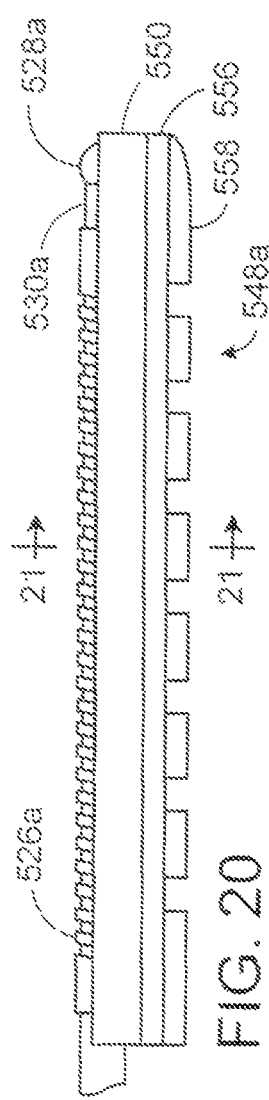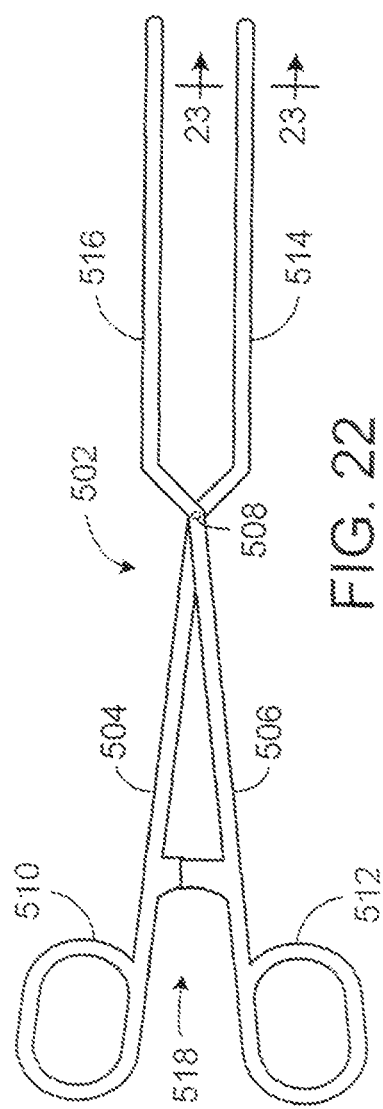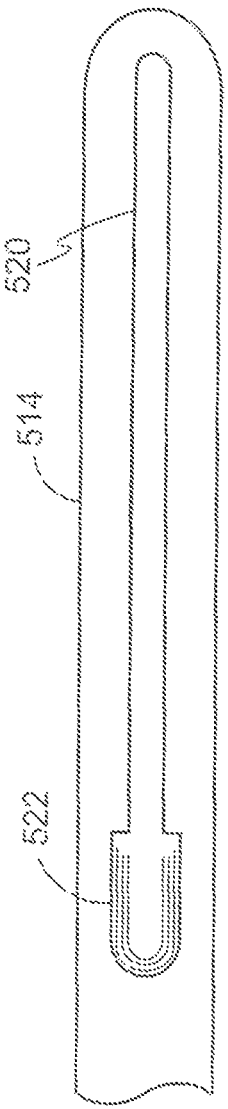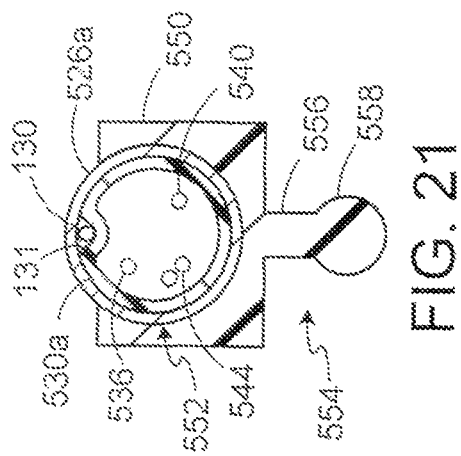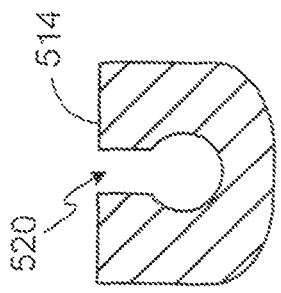

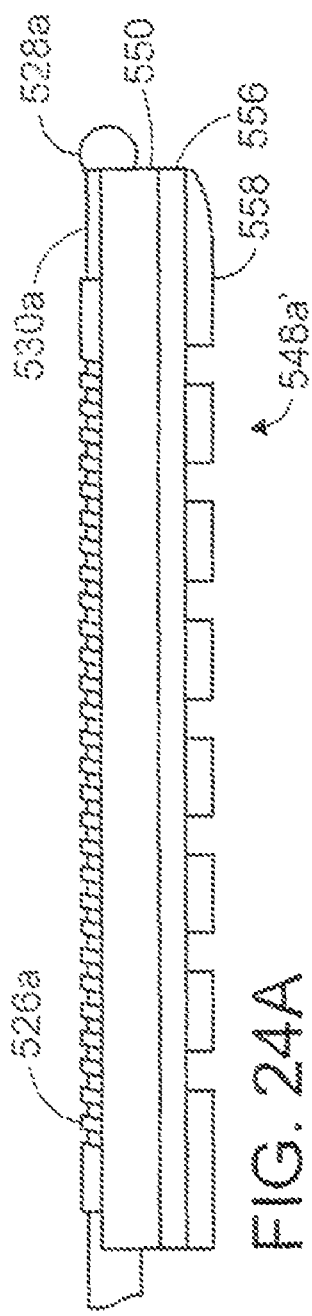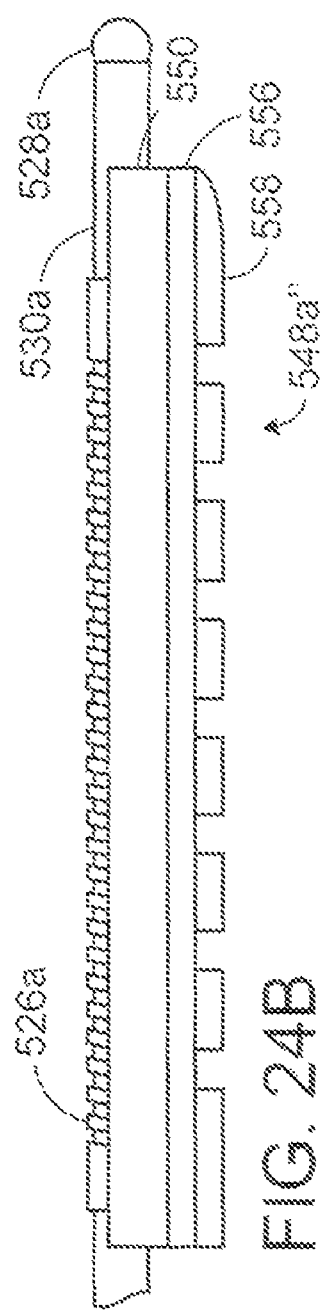

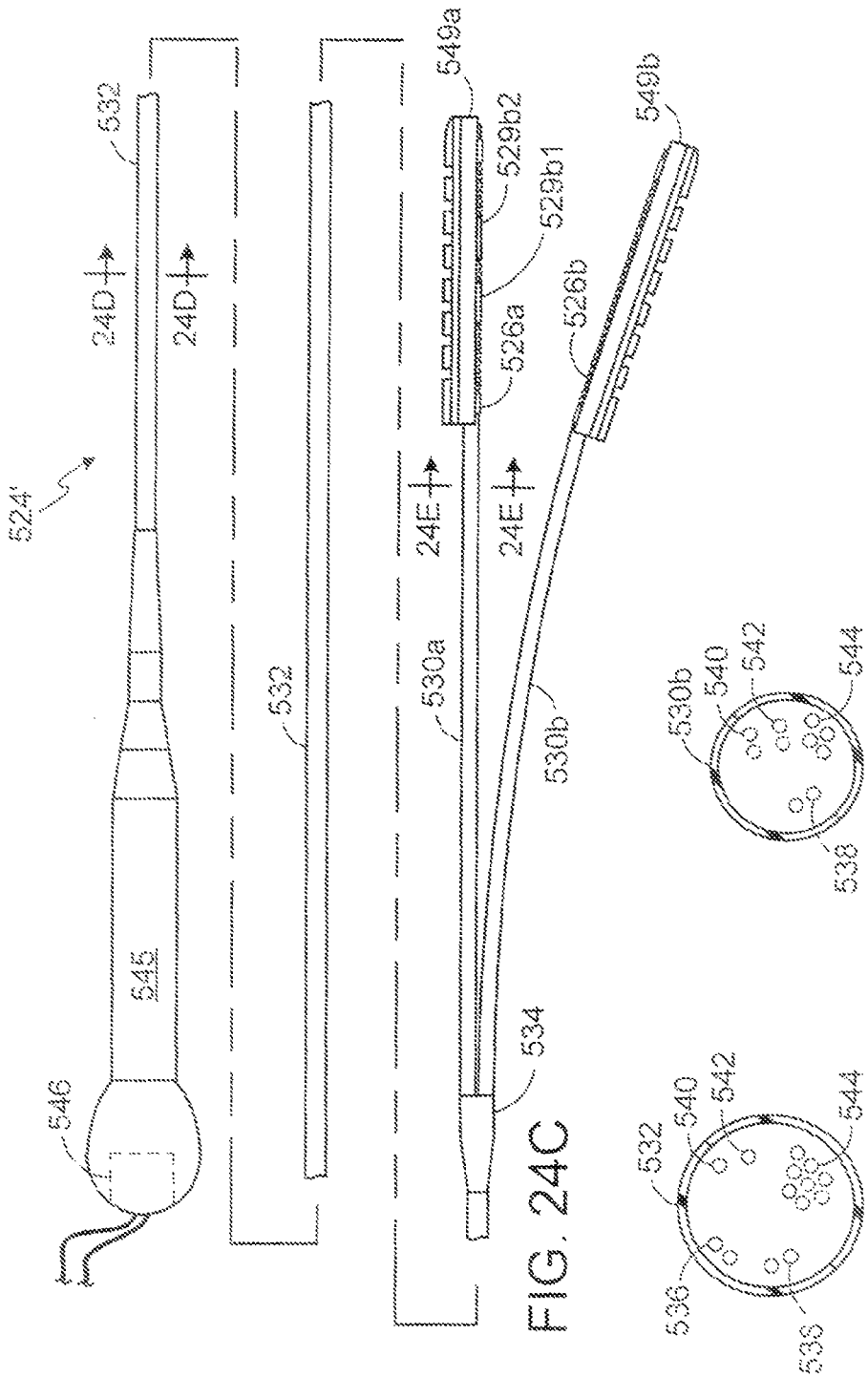

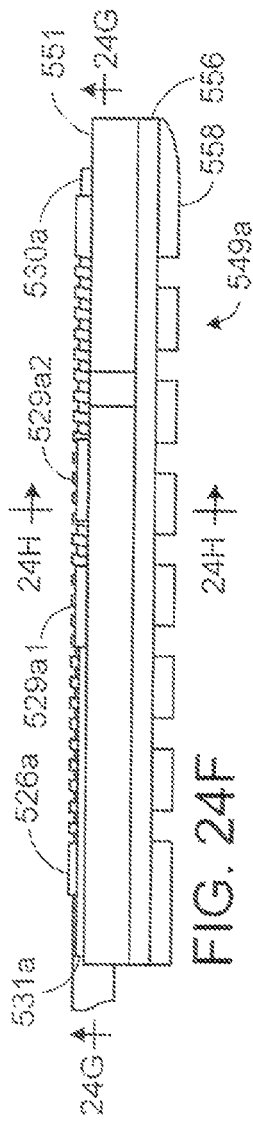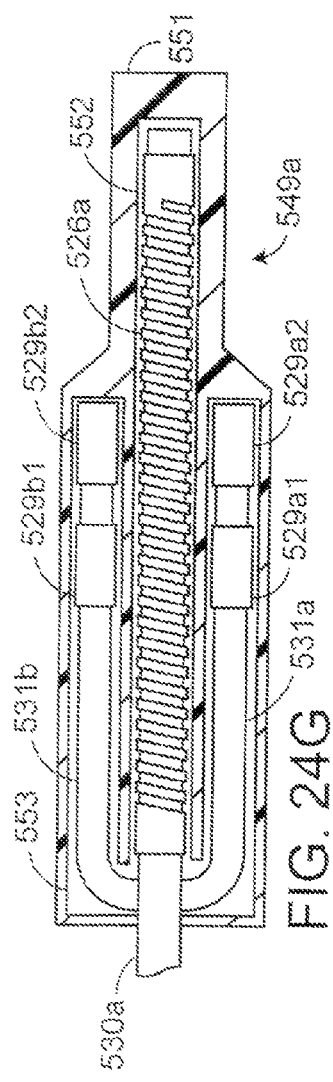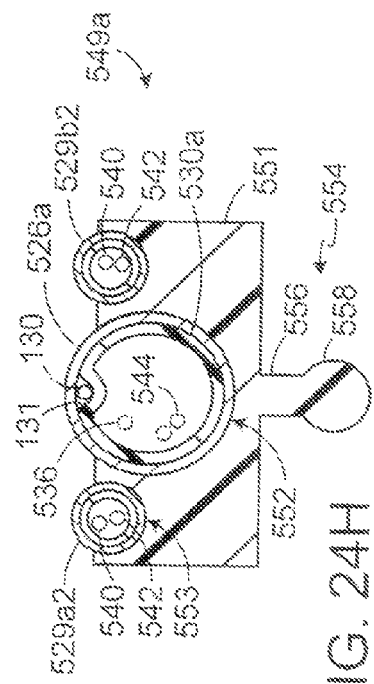

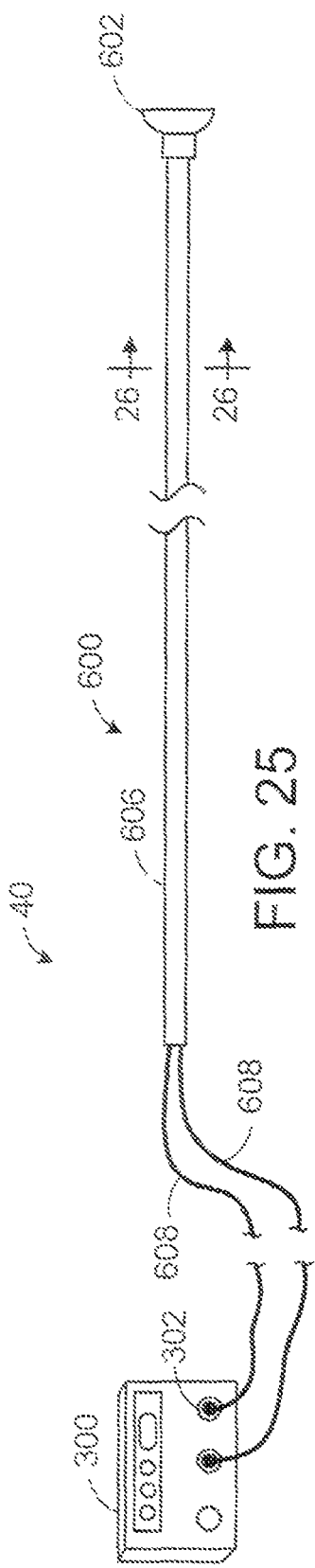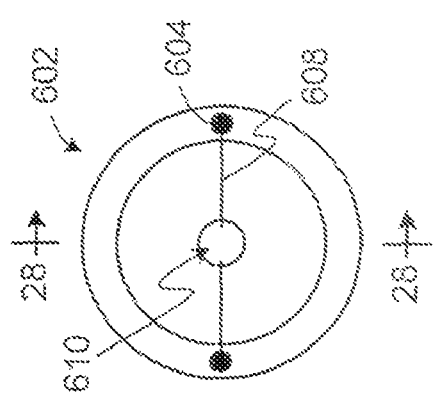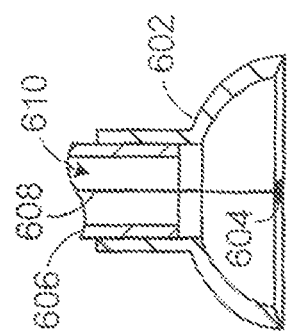

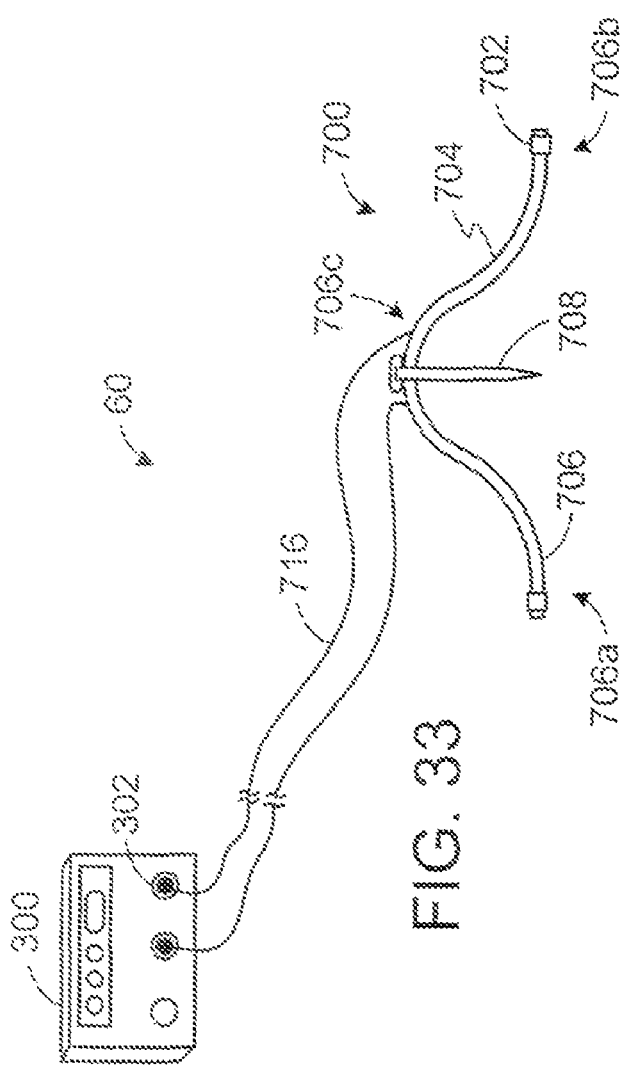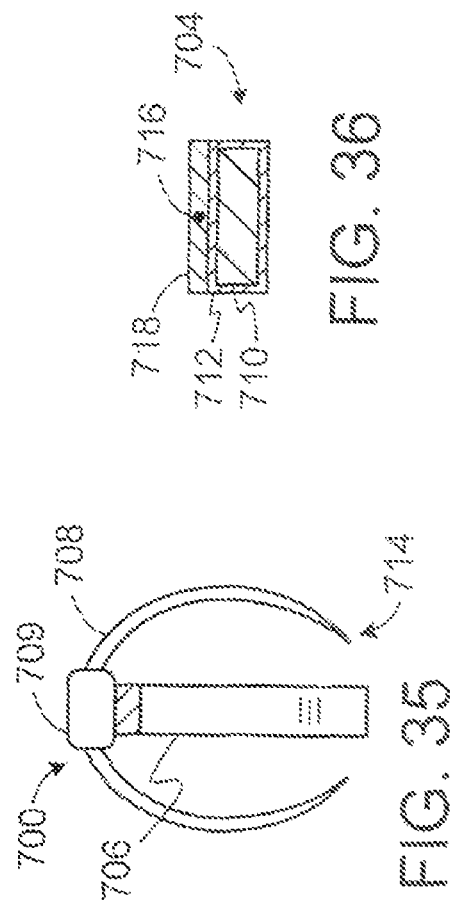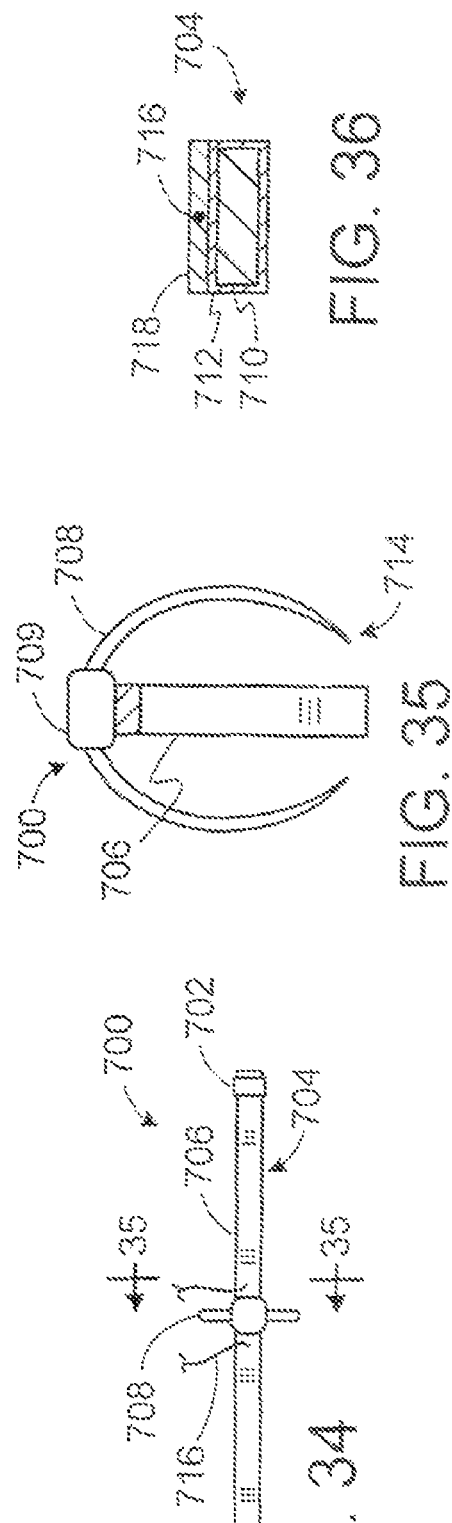

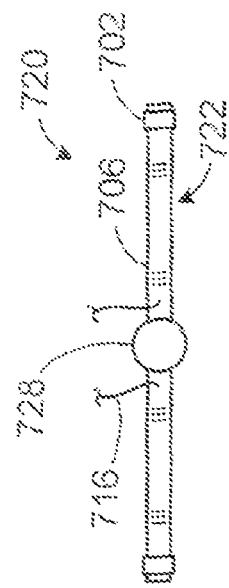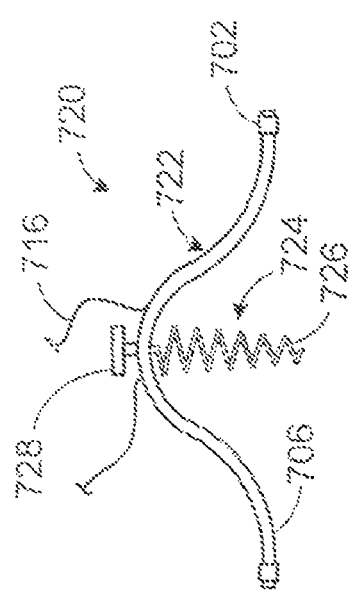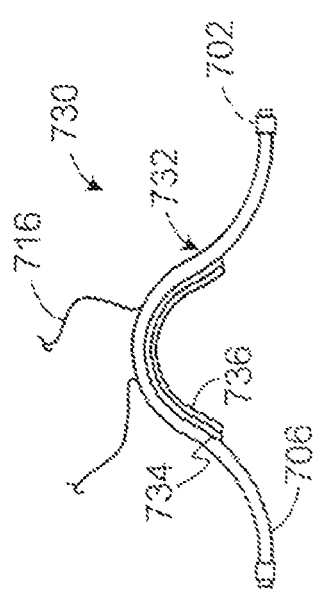

CLAMP BASED METHODS AND APPARATUS FOR FORMING LESIONS IN TISSUE AND CONFIRMING WHETHER A THERAPEUTIC LESION HAS BEEN FORMED

CROSS REFERENCE TO RELATED APPLICATION

This application is a continuation of U.S. patent application Ser. No. 10/727,144, filed Dec. 2, 2003, now issued as U.S. Pat. No. 8,002,770, entitled 'CLAMP BASED METHODS AND APPARATUS FOR FORMING LESIONS IN TISSUE AND CONFIRMING WHETHER A THERAPEUTIC LESION HAS BEEN FORMED," the entire disclosure of which is incorporated herein by reference for all purposes.

BACKGROUND OF THE INVENTIONS

1. Field of Inventions

The present inventions relate generally to surgical devices for forming therapeutic lesions.

2. Description of the Related Art

There are many instances where therapeutic elements must be inserted into the body. One instance involves the formation of therapeutic lesions to the treat cardiac conditions such as atrial fibrillation, atrial flutter and arrhythmia. Therapeutic lesions may also be used to treat conditions in other regions of the body including, but not limited to, the prostate, liver, brain, gall bladder, uterus and other solid organs. Typically, the lesions are formed by ablating tissue with one or more electrodes. Electromagnetic radio frequency ("RF") energy applied by the electrode heats, and eventually kills (i.e. "ablates"), the tissue to form a lesion. During the ablation of soft tissue (i.e. tissue other than blood, bone and connective tissue), tissue coagulation occurs and it is the coagulation that kills the tissue. Thus, references to the ablation of soft tissue are necessarily references to soft tissue coagulation. "Tissue coagulation" is the process of cross-linking proteins in tissue to cause the tissue to jell. In soft tissue, it is the fluid within the tissue cell membranes that jells to kill the cells, thereby killing the tissue.

Depending on the procedure, a variety of different electrophysiology devices may be used to position one or more coagulation electrodes at the target location. Each electrode is connected to a power supply and control apparatus and, in some instances, the power to the electrodes is controlled on an electrode-by-electrode basis. Examples of electrophysiology devices include catheters and surgical devices such as surgical probes and clamps. Catheters are relatively long, flexible devices that are configured to travel through a vein or artery until the coagulation electrodes carried on their distal portions reach the target tissue. The electrodes on the distal portions of surgical devices are, on the other hand, typically placed directly in contact with the targeted tissue area by a physician during a surgical procedure, such as open heart surgery, where access can be obtained by way of a thoracotomy, median sternotomy, or thoracostomy.

Catheters used to create lesions typically include a relatively long and relatively flexible body that has one or more coagulation electrodes on its distal portion. The portion of the catheter body that is inserted into the patient is typically from 23 to 55 inches in length and there may be another 8 to 15 inches, including a handle, outside the patient. The proximal end of the catheter body is connected to the handle which includes steering controls. The length and flexibility of the catheter body allow the catheter to be inserted into a main vein or artery (typically the femoral artery), directed into the interior of the heart, and then manipulated such that the electrode contacts the tissue that is to be ablated. Fluoroscopic imaging is used to provide the physician with a visual indication of the location of the catheter. Exemplary catheters are disclosed in U.S. Pat. No. 5,582,609.

Surgical probes used to create lesions often include a handle, a relatively short shaft that is from 4 inches to 18 inches in length and either rigid or relatively stiff, and a distal section that is from 1 inch to 10 inches in length and either malleable or somewhat flexible. One or more coagulation electrodes are carried by the distal section. Surgical probes are used in epicardial and endocardial procedures, including open heart procedures and minimally invasive procedures where access to the heart is obtained via a thoracotomy, thoracostomy or median sternotomy. Exemplary surgical probes are disclosed in U.S. Pat. No. 6,142,994.

Clamps, which have a pair of opposable clamp members that may be used to hold a bodily structure or a portion thereof, are another example of a surgical device that has been used to create lesions. Examples of clamps which carry coagulation electrodes are disclosed in U.S. Pat. No. 6,142,994. Such clamps are particularly useful when the physician intends to position electrodes on opposite sides of a body structure in a bipolar arrangement.

The inventor herein has determined that conventional apparatus and methods for forming therapeutic lesions are susceptible to improvement. For example, inventor herein has determined that conventional methods and apparatus for confirming whether a therapeutic lesion has been properly formed during surgical procedures are susceptible of improvement. The inventor herein has also determined that conventional methods and apparatus for securing stimulation and sensing electrodes to tissue during surgical procedures are susceptible of improvement.

SUMMARY OF THE INVENTIONS

Surgical devices in accordance with some embodiments of the present inventions include a tissue stimulation element that, in some instances, may also be used for sensing purposes. Some of the surgical devices also include a tissue coagulation element. The present surgical device provide a number of advantages over conventional surgical devices. For example, the some of the surgical devices may be used to form lesions and also used to determine whether or not a therapeutic lesion has been formed. The surgical devices may also be used to bring stimulation and sensing elements into contact with tissue in a manner that is superior to conventional methods.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 2 is a plan view of a surgical probe in accordance with a preferred embodiment of a present invention.

FIG. 3 is a section view taken along line 3-3 in FIG. 2.

FIG. 4 is a section view taken along line 4-4 in FIG. 2.

FIG. 5 is a section view taken along line 5-5 in FIG. 2.

FIG. 6 is an end view of the surgical probe illustrated in FIG. 2.

FIG. 6A is a perspective view of a surgical system in accordance with a preferred embodiment of a present invention.

FIG. 6B is a plan view of a portion of a surgical probe in accordance with a preferred embodiment of a present invention.

FIG. 7 is a perspective view of a surgical system in accordance with a preferred embodiment of a present invention.

FIG. 8 is a top view of a suction device in accordance with a preferred embodiment of a present invention.

FIG. 9 is a side view of the suction device illustrated in FIG. 8.

FIG. 10 is a bottom view of the suction device illustrated in FIG. 8.

FIG. 11 is a partial section view taken along line 11-11 in FIG. 9.

FIG. 12 is a section view taken along line 12-12 in FIG. 10.

FIG. 13 is a section view taken along line 13-13 in FIG. 10.

FIG. 17 is a plan view of a tissue coagulation and stimulation assembly in accordance with a preferred embodiment of a present invention.

FIG. 18 is a section view taken along line 18-18 in FIG. 17.

FIG. 19 is a section view taken along line 19-19 in FIG. 17.

FIG. 20 is an enlarged view of a portion of the tissue coagulation and stimulation assembly illustrated in FIG. 17.

FIG. 21 is a section view taken along line 21-21 in FIG. 20.

FIG. 22 is a plan view of a clamp in accordance with a preferred embodiment of a present invention.

FIG. 23 is a section view taken along line 23-23 in FIG. 22.

FIG. 24 is a top view of a portion of the clamp illustrated in FIG. 22.

FIG. 24A is a side view of a portion of a tissue coagulation and stimulation assembly in accordance with one embodiment of a present invention.

FIG. 24B is a side view of a portion of a tissue coagulation and stimulation assembly in accordance with one embodiment of a present invention.

FIG. 24C is an enlarged view of a portion of a tissue coagulation and stimulation assembly in accordance with one embodiment of a present invention.

FIG. 24D is a section view taken along line 24D-24D in FIG. 24C.

FIG. 24E is a section view taken along line 24E-24E in FIG. 24C.

FIG. 24F is an enlarged view of a portion of the tissue coagulation and stimulation assembly illustrated in FIG. 24C.

FIG. 24G is partial section view taken along line 24G-24G in FIG. 24F.

FIG. 24H is a section view taken along line 24H-24H in FIG. 24F.

FIG. 25 is a perspective view of a surgical system in accordance with a preferred embodiment of a present invention.

FIG. 26 is a section view taken along line 26-26 in FIG. 25.

FIG. 27 is an end view of a probe in accordance with one embodiment of a present invention.

FIG. 28 is a section view taken along line 28-28 in FIG. 27.

FIG. 33 is a perspective view of a surgical system in accordance with a preferred embodiment of a present invention.

FIG. 34 is a top view of a self-anchoring device in accordance with a preferred embodiment of a present invention.

FIG. 35 is a section view taken along line 35-35 in FIG. 34.

FIG. 36 is an enlarged section view taken along line 35-35 in FIG. 34.

FIG. 37 is a side view of a self-anchoring device in accordance with a preferred embodiment of a present invention.

FIG. 38 is a top view of the device illustrated in FIG. 37.

FIG. 39 is a side view of a self-anchoring device in accordance with a preferred embodiment of a present invention.

FIG. 40 is a top view of the device illustrated in FIG. 39.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:
 I. Introduction
 II. Surgical Probes
 III. Suction Devices For Use With Surgical Probes
 IV. Clamp Based Devices
 V. Coagulation Electrodes, Temperature Sensing And Power Control
 VI. Stimulation Electrodes And Lesion Confirmation
 VII. Tissue Stimulation And Sensing Probes
 VIII. Self-Anchoring Tissue Stimulation and Sensing Devices The section titles and overall organization of the present detailed description are for the purpose of convenience only and are not intended to limit the present inventions.

I. Introduction

Surgical devices in accordance with the present inventions include one or more tissue coagulation elements and/or one or more tissue stimulation elements. The tissue coagulation elements may be used to, for example, form therapeutic lesions and the tissue stimulation elements may be used to, for example, test whether or not the desired therapeutic lesion has been formed. The stimulation elements may also be used to stimulate tissue and sense electrical activity in tissue (such as by pacing and recording) during a surgical procedure. The surgical devices may be used in conjunction with power supply and control apparatus that supply and control power to the tissue coagulation elements in bipolar and/or unipolar modes. The surgical devices may also be used in conjunction with tissue stimulation apparatus, such as pacing and recording apparatus, which supply power that stimulates (but does not coagulate) tissue. Tissue stimulation may be used to confirm whether or not a therapeutic lesion has been formed by, for example, supplying tissue stimulation energy on one side of a lesion and/or monitoring tissue (either electrically or visually) on the other side of the lesion. Tissue stimulation may also be used to determine lesion depth and, correspondingly, whether or not a lesion is transmural.

II. Surgical Probes

Figure 1:
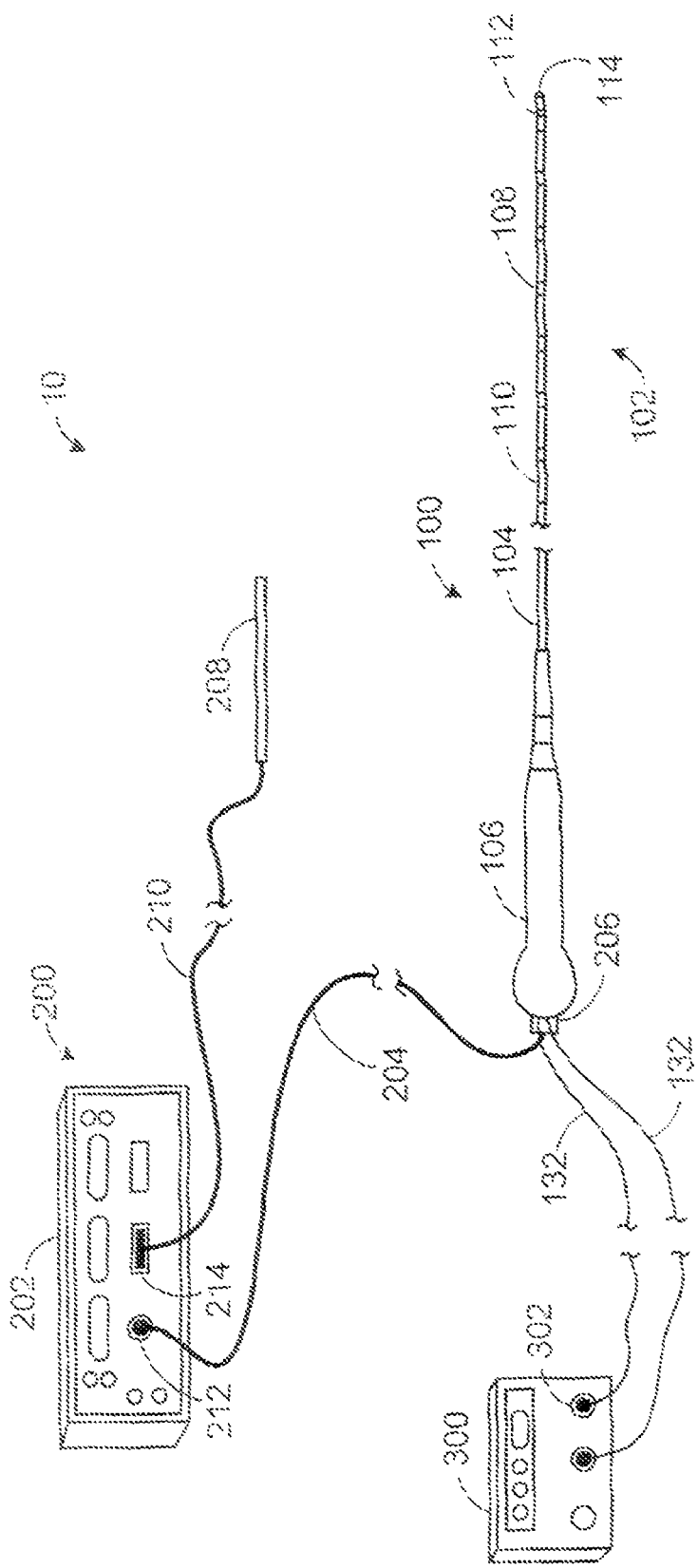
FIG. 1 is a perspective view of a surgical system in accordance with a preferred embodiment of a present invention.

As illustrated for example in FIG. 1, an exemplary surgical system 10 in accordance with one embodiment of a present invention includes a surgical probe 100, a power supply and control apparatus 200, and a tissue stimulation apparatus 300. The power supply and control apparatus 200 and tissue stimulation apparatus 300 are discussed in Sections V and VI below. The surgical probe 100 includes a relatively short shaft 102 with a proximal section 104, which is connected to a handle 106, and a distal section 108, on which coagulation electrodes 110 are supported. The coagulation electrodes 110 are discussed in Section V below. The distal section 108 also supports tissue stimulation electrodes 112 and 114. The tissue stimulation electrodes 112 and 114, which are discussed in Section VI below, may also be used to sense local tissue activation.

Turning to FIGS. 2-5, the exemplary shaft proximal section 104 consists of a hypotube 116, which is either rigid or relatively stiff, and an outer polymer tubing 118 over the hypotube. The handle 106 preferably consists of two molded handle halves and is provided with strain relief element 120. The shaft proximal section 104 in the illustrated embodiment may be from 4 inches to 18 inches in length and is preferably 6 inches to 8 inches. The shaft distal section 108, which is preferably either malleable, somewhat flexible or some combination thereof, may be from 1 inch to 10 inches in length and is preferably 3 to 5 inches.

As used herein the phrase "relatively stiff" means that the shaft (or distal section or other structural element) is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial. Rigid and somewhat flexible shafts are preferably formed from stainless steel, while malleable shafts are formed from annealed stainless steel. Additional information concerning "relatively stiff" shafts is provided in U.S. Pat. No. 6,142,994, which is incorporated herein by reference.

In those instances where a malleable shaft proximal portion 104 is desired, the hypotube 116 may be a heat treated malleable hypotube. By selectively heat treating certain portions of the hypotube, one section of the hypotube can be made more malleable than the other. The outer tubing 118 may be formed from Pebax® material, polyurethane, or other suitable materials.

As noted above, the shaft distal section 108 can be either somewhat flexible, in that it will conform to a surface against which it is pressed and then spring back to its original shape when removed from the surface, malleable, or some combination thereof. In the exemplary implementation illustrated in FIGS. 1-7, the distal section 108 includes a malleable proximal portion and a flexible distal portion. Although the relative lengths of the portions may vary to suit particular applications, the malleable proximal portion and a flexible distal portion are equal in length in the illustrated embodiment.

Referring more specifically to FIGS. 4 and 5, the exemplary shaft distal section 108 includes an outer member 122 that carries the electrodes 110-114. The outer member 122 is a flexible tubular structure which has an outer diameter that is, depending on the diameter of the electrodes 110 and 112, typically between about 2 mm and about 4 mm. The outer member 122 in the illustrated embodiment, which is intended for use in cardiovascular applications, typically has an outer diameter of about 3 mm. Suitable support structure materials include, for example, flexible biocompatible thermoplastic tubing such as unbraided Pebax® material, polyethylene, or polyurethane tubing.

Turning to the interior of the shaft distal section 108, the exemplary malleable portion includes a mandrel 124 (FIG. 4) made of a suitably malleable material, such as annealed stainless steel or beryllium copper, that may be fixed directly within the distal end of the shaft's hypotube 116 and secured by, for example, soldering, spot welding or adhesives. Sufficient space should be provided to allow passage of the power lines 126, which are connected to the coagulation electrodes 110, the temperature sensor signal lines 128, which are connected to temperature sensors 130 (FIG. 5) such as thermocouples or thermistors, and signal lines 132, which are connected to the tissue stimulation electrodes 112 and 114. As described in greater detail below, the power lines 126 may be used to transmit energy from the power supply and control apparatus 200 to the coagulation electrodes 110, while signal lines 128 return temperature information from the temperature sensors 130 to the power supply and control apparatus. The signal lines 132 may be used to transmit tissue stimulation energy from the tissue stimulation apparatus 300 to the stimulation electrodes 112 and 114. The signal lines 132 may also be used to transmit the signals associated with local electrical activity when the tissue stimulation electrode 112 and 114 are used for sensing. An insulating sleeve 134 is placed over the mandrel 124 to protect the power lines 126, temperature sensor signal lines 128 and signal lines 132. The insulating sleeve 134 is preferably formed from Pebax® material, polyurethane, or other suitable materials.

With respect to the flexible portion, a spring member 136, which is preferably either a solid flat wire spring (FIG. 5), a round wire, or a three leaf flat wire Nitinol® spring, is connected to the distal end of the mandrel 124 with a crimp tube or other suitable instrumentality. The distal end of the spring member 136 is connected to the electrode 114 by, for example, an adhesive that will also electrically insulate the spring member from the electrode. The electrode 114 is also secured to the distal end of the outer member 122. Other spring members, formed from materials such as 17-7 or carpenter's steel, may also be used. The spring member 136 is also enclosed within the insulating sleeve 134. The spring member 136 may be pre-stressed so that the distal tip is pre-bent into a desired shape. Additional details concerning distal sections that have a malleable proximal portion and a flexible distal portion are provided in U.S. Pat. No. 6,464,700, which is incorporated herein by reference.

In an alternative configuration, the distal section 108 may be formed by a hypotube that is simply a continuation of the shaft hypotube 116 covered by a continuation of the outer tubing 118. However, the distal end hypotube can also be a separate element connected to the shaft hypotube 116, if it is desired that the distal end hypotube have different stiffness (or bending) properties than the shaft hypotube. It should also be noted that the distal section 108 may be made malleable from end to end by eliminating the spring member 136 and extending the malleable mandrel 124 to the electrode 114. Conversely, the distal section 108 may be made flexible from end to end by eliminating the malleable mandrel 124 and extending the spring member 136 from the hypotube 116 to the electrode 114.

Turning to FIGS. 5 and 6, the power lines 126 and signal lines 128 extend from the coagulation electrodes 110 and temperature sensors 130 to a connector (such as the exemplary PC board 138) that is carried by the handle 106. The handle 106 also includes a port 140 that is configured to receive a connector, such as the connector 206 (FIG. 1) from the power supply and control apparatus 200, for connection to the PC board 138. Openings 142 and 144 are provided for the signal lines 132.

The exemplary surgical system 11, which is illustrated in FIGS. 6A and 6B, includes a surgical probe 101, a power supply and control apparatus 200, a tissue stimulation apparatus 300 and an EP recording apparatus 301. The power supply and control apparatus 200 is discussed in Section V, while the tissue stimulation apparatus 300 and EP recording apparatus 301 are discussed in Section VI. The exemplary surgical probe 101 is essentially identical to the surgical probe 100 and similar elements are represented by similar reference numerals. Here, however, a plurality of stimulation electrodes 112 are located along the length of the shaft distal portion 108. In the illustrated embodiment, a stimulation electrode 112 is located between each of the coagulation electrodes 110. There is also a stimulation electrode 112 proximal of the proximal-most coagulation electrode 110 and a stimulation electrode 112 distal of the distal-most coagulation electrode 110. A stimulation electrode 114 is also provided on the distal end of the probe. Signal lines 132, which are connected to the tissue stimulation electrodes 112 and 114, extend though a cable 115 and are connected to the EP recording apparatus 301 with a connector 117.

In another alternative implementation, pairs of stimulation electrodes 112 may be located between each of the coagulation electrodes 110, proximal of the proximal-most coagulation electrode, and distal of the distal-most coagulation electrode. A stimulation electrode 114 on the distal end of the probe may also be provided.

III. Suction Devices for Use with Surgical Probes

As illustrated for example in FIG. 7, an exemplary surgical system 20 in accordance with one embodiment of a present invention includes a surgical probe 100', a power supply and control apparatus 200, a tissue stimulation apparatus 300 and an EP recording apparatus 301. The power supply and control apparatus 200 is discussed in Section V, while the tissue stimulation apparatus 300 and EP recording apparatus 301 are discussed in Section VI. The exemplary system is also provided with a suction apparatus 400 that includes a suction source 402 and a suction device 404 that may be removably secured to the distal section 108 of the surgical probe 100'. The suction device 404 is connected to the suction source 402 by a flexible tube 406. When the suction source 402 is actuated, the suction device 404 will fix the position of the distal section of the surgical probe 100' relative to the target tissue. Additionally, depending on the rigidity of the suction device 404 and the rigidity of the tissue, the applied vacuum may also cause the tissue and electrodes 110 on the distal section 108 to come into contact with one another because portions of the suction device will deflect, portions of the tissue surface will deflect, or portions of both the suction device and the tissue surface will deflect.

The surgical probe 100' is substantially identical to surgical probe 100 and similar elements are represented by similar reference numerals. Surgical probe 100' does not, however, include the tissue stimulation electrodes 112 and 114. Instead, as illustrated in FIG. 10, the suction device 404 is provided with tissue stimulation electrodes 426 and, in some instances, sensing electrodes 428. The tissue stimulation and sensing electrodes 426 and 428, which are held firmly against tissue when the suction source 402 is activated, are discussed in Section VI below.

The exemplary suction source 402 may be any suitable device that is capable of supplying the desired partial vacuum, which will typically range from about 200 mmHg to about 700 mmHg. Turning to FIGS. 8-13, the exemplary suction device 404 includes a main body 407, a pair of internal suction lines 408 and a plurality of individual suction ports 410. The suction tube 406 may be connected to the internal suction lines 408 by a connector 412 such as, for example, the illustrated Luer connector. The suction ports 410 are respectively connected to the internal suction lines 408 by a plurality of apertures 414. The suction ports 410 are also formed in the curved bottom surface 416 (or "bottom wall") of the main body 407 and define respective suction regions 418 (FIG. 12). During use, the curved bottom surface will form a seal with the tissue surface and air within the suction regions 418 will be drawn through the apertures 414, thereby causing the suction device 404 to adhere to the tissue surface.

Figure 14:
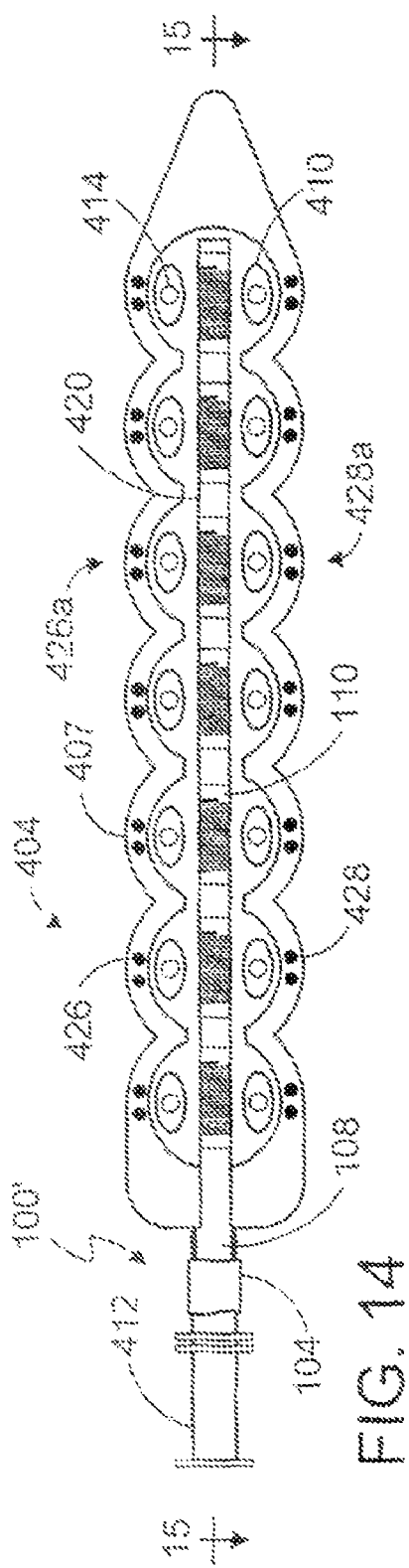
FIG. 14 is a bottom view of showing a portion of the surgical system illustrated in FIG. 7.
Figure 15:
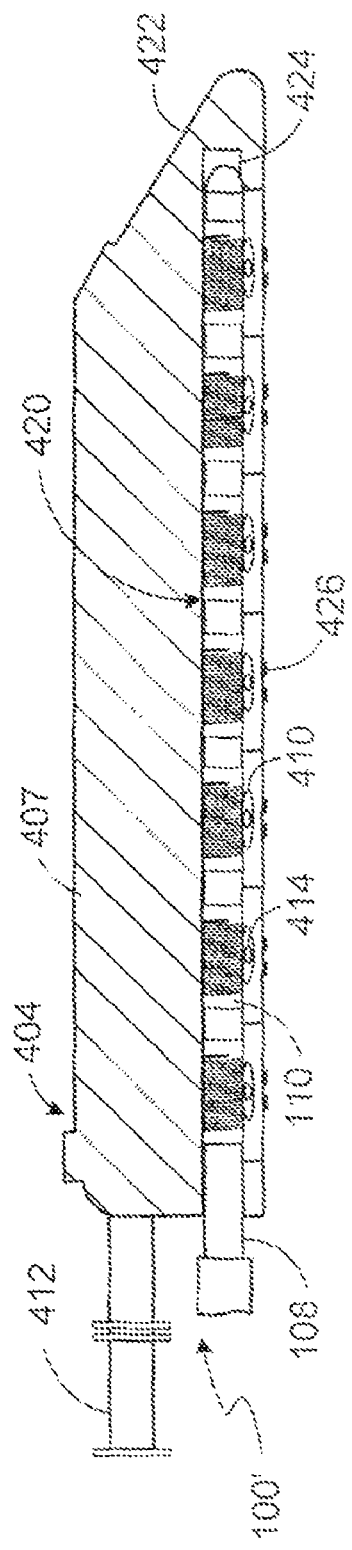
FIG. 15 is a partial section view taken along line 15-15 in FIG. 14.

The suction device 404 also includes a connector that enables it to be removably secured to the distal portion 108 of the surgical probe 100'. Although the present inventions are not limited to any particular connector, the connector in the exemplary embodiment is a slot 420 into which the surgical probe distal portion 108 may be inserted. The slot 420 is generally semi-circular in cross-section and extends between about 180 to 360 degrees, and preferably about 300 degrees. The diameter of the slot 420 will preferably be about the same as the diameter of the surgical probe distal portion 108. As such, the distal portion 108 may be removably snap fit into the slot 420. Additionally, once the surgical probe distal portion 108 is within the slot 420, it may be advanced distally toward the suction device nose 422 and into an aperture 424 for anchoring (FIGS. 14 and 15).

The specific size and shape of the suction device 404 will, of course, depend on the intended application, as will the choice of materials. Although the present inventions are not limited to any particular sizes, shapes or materials, one exemplary implementation that is especially well suited for cardiac treatment and use with the above-described surgical probe 100' is described hereafter. The suction device 404 is formed, preferably by molding, from a soft, flexible biocompatible material such as silicone rubber or urethane that is capable of withstanding temperatures up to 120° C. without melting or burning. When molded, the suction device 404 will be an integrally formed (i.e. one piece) structure, although some or all of the connector 412 may be added after molding depending on the type of connector employed. The overall length of the suction device 404, not including the connector 412, will be slightly longer than the shaft distal portion 108, e.g. about 10 cm in an exemplary implementation where the distal portion is about 9 cm.

The exemplary suction ports 410 are generally concave and elliptical in shape and have a major diameter of about 5 mm, a minor diameter of about 3 mm, a depth of about 2 mm. In the illustrated embodiment, the spacing corresponds to the spacing of the electrodes on the associated probe. Alternatively, the exemplary elliptical (i.e. 5 mm×3 mm×2 mm) suction ports may be spaced apart by about 6 mm center-to-center. The distance between the bottom of the slot 420 and the bottom of the main body 407 is about 5 mm. This exemplary configuration will result in the surgical probe 100' and suction device 404 mating with one another in the manner illustrated in FIGS. 14 and 15.

With respect to the electrical connection of the stimulation electrodes 426 to the tissue stimulation apparatus 300 and EP recording apparatus 301, and referring to FIGS. 12 and 13, the stimulation electrodes in the exemplary implementation are connected to signal lines 430 that extend from the stimulation electrodes, around the main body 407, to a signal line bundle 432 on the top of the main body. Similarly, signal lines 434 extend from the sensing electrodes 428 to a signal line bundle 436. A silicone rubber overmold 438 may be used to cover the individual signal lines and signal line bundles in those instances where the main body 407 is formed from silicone rubber. Alternatively, in those instances where the main body is formed from polyurethane, the signal lines and signal line bundles may be held in place with an elastic polyurethane adhesive. The signal lines in the bundles 432 and 436 pass through a cable 440 (FIG. 7) and are connected to the EP recording apparatus 301 by a connector 442. As discussed below, the EP recording apparatus 301 is connected to, and directs the tissue stimulation and recording associated with, the tissue stimulation apparatus 300.

It should also be noted that, instead of the exemplary surgical probe 100', the exemplary suction device 404 may be secured to the distal portion of a conventional electrophysiology catheter. The distal portion of the catheter and suction device 404 could then be used to directly place electrodes against tissue during a surgical procedure. The exemplary suction device 404 may also be permanently secured to a surgical probe or catheter by overmolding the suction device onto the surgical probe or catheter.

IV. Clamp Based Devices

Figure 16:
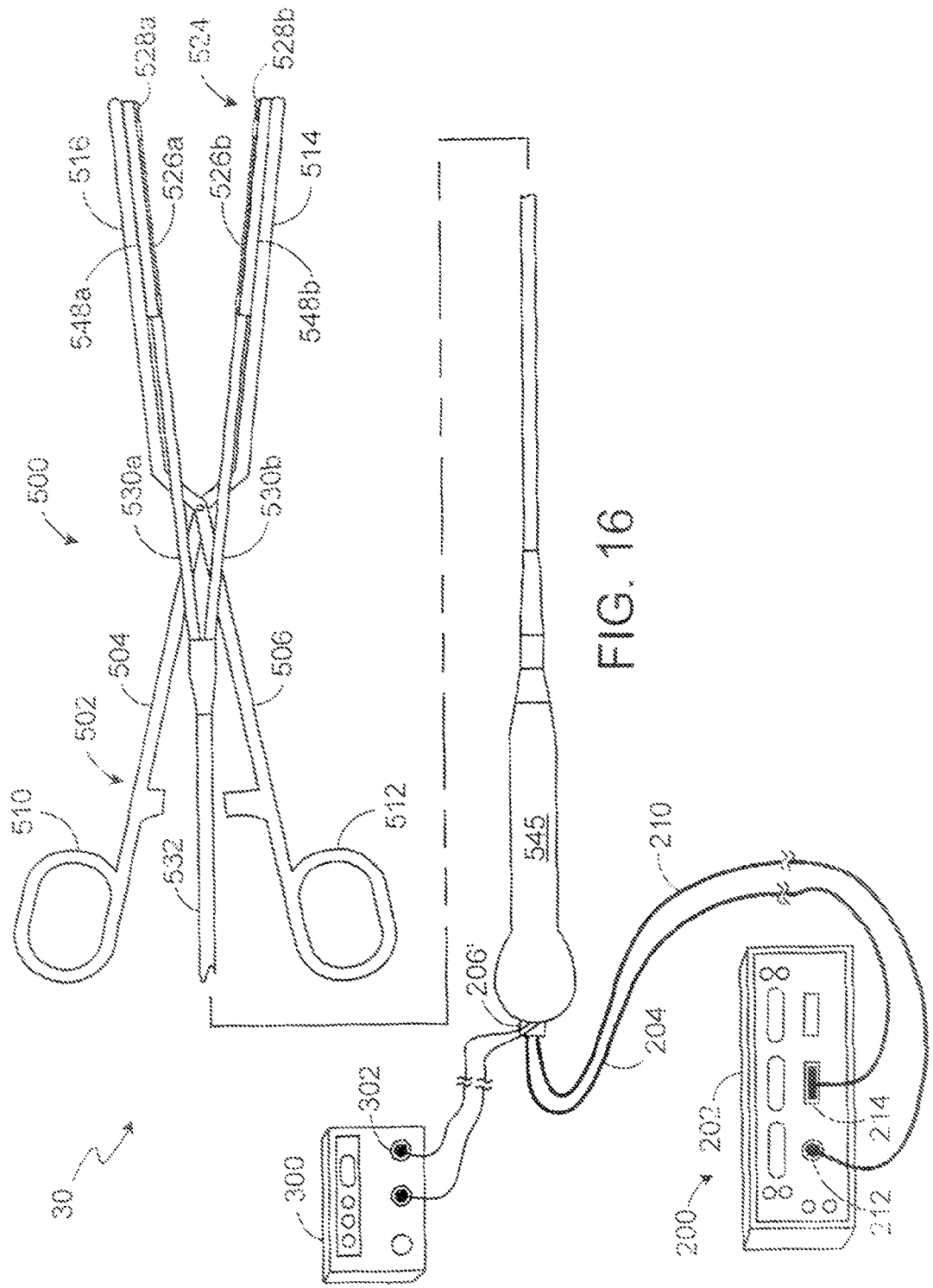
FIG. 16 is a perspective view of a surgical system in accordance with a preferred embodiment of a present invention.

As illustrated for example in FIG. 16, an exemplary surgical system 30 in accordance with one embodiment of a present invention includes an electrophysiology clamp apparatus 500, a power supply and control apparatus 200, and a tissue stimulation apparatus 300. The power supply and control apparatus 200 and tissue stimulation apparatus 300 are discussed in Sections V and VI below. The electrophysiology clamp apparatus 500 includes a clamp and a tissue coagulation and stimulation assembly that may be secured to the clamp. As used herein, the term "clamp" includes, but is not limited to, clamps, clips, forceps, hemostats, and any other surgical device that includes a pair of opposable clamp members that hold tissue, at least one of which is movable relative to the other. In some instances, the clamp members are connected to a scissors-like arrangement including a pair of handle supporting arms that are pivotably connected to one another. The clamp members are secured to one end of the arms and the handles are secured to the other end. Certain clamps that are particularly useful in minimally invasive procedures also include a pair of handles and a pair of clamp members. Here, however, the clamp members and handles are not mounted on the opposite ends of the same arm. Instead, the handles are carried by one end of an elongate housing and the clamp members are carried by the other. A suitable mechanical linkage located within the housing causes the clamp members to move relative to one another in response to movement of the handles. The clamp members may be linear or have a predefined curvature that is optimized for a particular surgical procedure or portion thereof. The clamp members may also be rigid or malleable.

One example of a clamp is generally represented by reference numeral 502 in FIGS. 16 and 22-24. Referring more specifically to FIGS. 22-24, the clamp 502 includes a pair of rigid arms 504 and 506 that are pivotably connected to one another by a pin 508. The proximal ends of the arms 504 and 506 are respectively connected to a pair handle members 510 and 512, while the distal ends are respectively connected to a pair of clamp members 514 and 516. The clamp members 514 and 516 may be rigid or malleable and, if rigid, may be linear or have a pre-shaped curvature. A locking device 518 locks the clamp in the closed orientation, and prevents the clamp members 514 and 516 from coming any closer to one another than is illustrated in FIG. 22, thereby defining a predetermined spacing between the clamp members. The clamp 502 is also configured for use with a pair of soft, deformable inserts (not shown) that may be removably carried by the clamp members 514 and 516 and allow the clamp to firmly grip a bodily structure without damaging the structure. To that end, the clamp members 514 and 516, each include a slot 520 (FIGS. 23 and 24) that is provided with a sloped inlet area 522 and the inserts include mating structures that are removably friction fit within the slots. The present tissue coagulation and stimulation assemblies may be mounted on the clamp members in place of the inserts.

One example of a tissue coagulation and stimulation assembly, which is generally represented by reference numeral 524 in FIGS. 16-19, includes first and second tissue coagulation electrodes 526a and 526b, which are discussed in Section V below, and first and second tissue stimulation electrodes 528a and 528b, which are discussed in Section VI below. Typically, there will be about 1 to 3 mm between the distal ends of the coagulation electrodes 526a and 526b and the stimulation electrodes 528a and 528b. The electrodes are carried on support structures 530a and 530b, which are connected to a flexible cable 532 by a molded plastic junction 534. The first and second coagulation electrodes 526a and 526b are also relatively long electrodes (e.g. about 3 to 8 cm) and, to that end, power lines 536 are connected to each longitudinal end of the first tissue coagulation electrode 526a and return lines 538 are connected to each longitudinal end of the second tissue coagulation electrode 526b. It should be noted that although the return lines 538 may be used to return power when the surgical system 30 is operating in a bipolar mode, the return lines may also be used to supply power when the system is operating in a unipolar mode.

The tissue stimulation electrode 528a is connected to a signal line 540, and the tissue stimulation electrode 528b is connected to a signal line 542. The signal lines 540 and 542 may be used for transmission and return, respectively, when the system is being operated in a bipolar mode, and both may be used for transmission when the system is being operated in unipolar mode. The first and second tissue stimulation electrodes 528a and 528b, as well as the signal lines 540 and 542, may also be used to transmit signals when the stimulation electrodes are used for sensing and recording purposes.

In the exemplary embodiment, a plurality of temperature sensors 130 (FIG. 21), such as thermocouples or thermistors are carried on the support structures 530a and 530b. There are four (4) temperature sensors 130 associated with each tissue coagulation electrode 526a and 526b in the exemplary embodiment. Signal lines 544 are connected to each of the temperature sensors 130.

In an alternative arrangement, one or both of the first and tissue second coagulation electrodes 526a and 526b may be split into two electrodes that are about 1.5 cm to 4 cm in length and separated by about 1 to 3 mm. Here, each electrode will be connected to a single power or return line and two temperature sensors 130 will be associated with each electrode.

As described in greater detail below, the power supply lines 536 may be used to transmit energy from the power supply and control apparatus 200 to the coagulation electrode 526a (which is returned by way of coagulation electrode 526b and return lines 538), while the signal lines 544 return temperature information from the temperature sensors 130 to the power supply and control apparatus. The signal line 540 may be used to transmit tissue stimulation energy from the tissue stimulation apparatus 300 to the stimulation electrode 528a. The stimulation energy is returned to the tissue stimulation apparatus 300 by way of the stimulation electrode 528b and signal line 542. The power supply and return lines 536 and 538 and signal lines 540-544 extend from the electrodes 526a-528b and temperature sensors 130, through the cable 532, to a handle 545. The power supply and return lines 536 and 538 and signal lines 544 are connected to a PC board 546 that is carried by the handle 545. The handle 545 also includes a port (not shown) for a connector 206' from the power supply and control apparatus 200 which connects to the PC board 546, and openings (not shown) for signal lines 540 and 542, which are connected to the tissue stimulation apparatus 300.

The exemplary tissue coagulation and stimulation assembly 524 also includes a pair of base members 548a and 548b which are used to connect the assembly to the clamp 502. Although the configuration of the energy transmission and stimulation assembly may vary from application to application to suit particular situations, the exemplary energy transmission and stimulation assembly 524 is configured such that the electrodes 526a and 526b will be parallel to one another as well as relatively close to one another (i.e. a spacing of about 1-10 mm) when the clamp 502 is in the closed orientation. The stimulation electrodes 528a and 528b will typically be about 5 mm to 50 mm apart when the clamp 502 is opened (in full or in part). Such an arrangement will allow the energy transmission and stimulation assembly to grip a bodily structure without cutting through the structure. Referring more specifically to FIGS. 20-24, the base member 548a includes a main portion 550, with a groove 552 that is configured to receive the support structure 530a and electrode 526a, and a connector 554 that is configured to removably mate with the slot 520 in the clamp 502. [It should be noted that the configuration of the base member 548b is identical to that of the base member 548a in the illustrated embodiment.] About 20% of the electrode surface (i.e. about 75° of the 360° circumference) is exposed in the illustrated embodiment. Adhesive may be used to hold the electrode 526a and support structure 530a in place. The exemplary connector 554 is provided with a relatively thin portion 556 and a relatively wide portion 558, which may consist of a plurality of spaced members (as shown) or an elongate unitary structure, in order to correspond to the shape of the slot 520.

The base members 548a and 548b are preferably formed from polyurethane. The length of the base members in the exemplary energy transmission assemblies will vary according to the intended application. In the area of cardiovascular treatments, it is anticipated that suitable lengths will range from, but are not limited to, about 4 cm to about 10 cm. In the exemplary implementation, where the electrodes 526a and 526b are preferably about 6.4 cm, the base members 548a and 548b will be about 6.6 cm.

The exemplary clamp apparatus 500 is not limited to the exemplary implementation described above and is susceptible to a wide variety of modifications. By way of example, and referring to FIGS. 24A and 24B, the tissue coagulation and stimulation assembly may be modified such that the position of the first and second tissue stimulation electrodes 528a and 528b relative to the first and tissue second coagulation electrodes 526a and 526b and/or the distal ends of the base members may be varied, as they are in base members 548a' and 548a".

Other exemplary clamp apparatus include a tissue coagulation and stimulation assembly wherein a plurality of stimulation electrodes are associated with one (or both) of coagulation electrodes. The stimulation electrodes may, for example, be located on opposite sides of a coagulation electrode so that the stimulation electrodes will be on opposite side of the lesion for stimulation and sensing purposes. One such tissue coagulation and stimulation assembly is generally represented by reference numeral 524' and is illustrated in FIGS. 24C-H. The tissue coagulation and stimulation assembly 524' is substantially similar to the tissue coagulation and stimulation assembly 524 illustrated in FIGS. 17-21 and similar elements are represented by similar reference numerals. Here, however, pairs of stimulation electrodes 529a1/529a2 and 529b1/529b2 are positioned on opposite sides of the coagulation electrode 526a. The spacing between the stimulation electrodes 529a1/529a2 and 529b1/529b2, which are discussed in Section VI below, and the coagulation electrode 526a will typically be about 1 mm. The coagulation electrodes 526a and 526b are carried on support structures 530a and 530b. The stimulation electrodes 529a1/529a2 and 529b1/529b2 are carried on support structures 531a and 531b.

The exemplary tissue coagulation and stimulation assembly 524' also includes a pair of base members 549a and 549b which are used to connect the assembly to the clamp 502 in the manner described above with reference to base members 548a and 548b. Referring more specifically to FIGS. 24F-24G, the base member 549a includes a main portion 551, with a groove 552 that is configured to receive the support structure 530a and electrode 526a, and a pair of grooves 553 that are configured to receive the stimulation electrodes 529a1/529a2 and 529b1/529b2 and support structures 531a and 531b. A connector 554 is configured to removably mate with the slot 520 in the clamp 502. The configuration of the base member 549b is identical to that of the base member 548b in the illustrated embodiment. Alternatively, the base member 549b may be configured to carry stimulation electrodes in the same manner as base member 549a. Still another alternative is to configure the assembly such that stimulation electrodes 529a1/529a2 are carried base member 549a, stimulation electrodes 529b1/529b2 are carried base member 549b, and stimulation electrodes 529a1/529a2 and stimulation electrodes 529b1/529b2 are on opposite side of the coagulation electrodes.

The tissue stimulation electrodes 529a1/529a2 are connected to respective signal lines 540 and 542, as are the tissue stimulation electrodes 529b1/529b2. The signal lines 540 and 542 may be used for transmission and/or return depending upon the manner in which the electrodes are being used. For example, the stimulation electrodes 529a1/529a2 may be used in bipolar mode to transmit stimulation energy and the stimulation electrodes 529b1/529b2 may be used in bipolar mode to sense local activation.

Finally, the clamp and the tissue coagulation and stimulation assemblies described above may be combined into an integral unit that cannot be readily separated. For example, the base members may be molded onto the clamp members. Such base members would, for example, extend completely around the each clamp member and/or include portions that are molded into the slots.

V. Coagulation Electrodes, Temperature Sensing and Power Control

In each of the surgical systems illustrated in FIGS. 1-24H, coagulation electrodes adapted to transmit RF energy are employed. However, other types of coagulation elements, such as such as lumens for chemical ablation, laser arrays, ultrasonic transducers, microwave electrodes, ohmically heated hot wires, and the like may be substituted for the coagulation electrodes. Coagulation electrodes may be arranged as a series of spaced electrodes or, alternatively, a single elongate coagulation electrode may be employed.

Although the present inventions are not limited to any particular number, the exemplary surgical probes 100, 100' and 101 illustrated in FIGS. 1-15 each include seven spaced coagulation electrodes 110, while the various clamp apparatus 500 illustrated in FIGS. 16-24H includes a single electrode 526a/526b carried on each of the clamp members 514 and 516. The coagulation electrodes are preferably in the form of wound, spiral closed coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. Preferred coil coagulation electrodes are disclosed in U.S. Pat. Nos. 5,797,905 and 6,245,068.

Alternatively, the coagulation electrodes 110 may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel, silver or titanium can be applied. The coagulation electrodes can also be in the form of helical ribbons. The electrodes can also be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks. Open coil electrodes may also be employed for coagulation.

The exemplary flexible coagulation electrodes 110 carried by the surgical probes 100, 100' and 101 illustrated in FIGS. 1-15 are preferably about 4 mm to about 20 mm in length. In the preferred embodiments, the electrodes are 12.5 mm in length with 1 mm to 3 mm spacing, which will result the creation of continuous lesion patterns in tissue when coagulation energy is applied simultaneously from adjacent electrodes through tissue to an indifferent electrode. For rigid coagulation electrodes, the length of the each electrode can vary from about 2 mm to about 10 mm. Using multiple rigid electrodes longer than about 10 mm each adversely effects the overall flexibility of the device, while electrodes having lengths of less than about 2 mm do not consistently form the desired continuous lesion patterns. The diameter, whether flexible or rigid, will typically be about 3 mm. Turning to the relatively long coagulation electrodes 526a and 526b carried by the clamp 502 illustrated in FIGS. 16-24H, for cardiovascular applications, the length is preferably between about 2 cm and 8 cm in those instances where power is supplied at both longitudinal ends of each electrode, and the end to end resistance is about 5 ohm to about 15 ohm. The diameter of the electrodes described above preferably ranges from about 1.5 mm to about 3 mm for cardiovascular applications and, in one preferred implementation, the outer diameter is about 2 mm.

In the exemplary embodiments, the temperature sensors 130 are preferably located within a linear channel, such as the channel 131 in FIG. 5, which is formed in the shaft distal portion 108 (FIGS. 1-15) or in the channel 131 in FIG. 21, which is formed in the support structures 530a and 530b (FIGS. 16-21 and 24C-24H). The linear channel insures that the temperature sensors will all face in the same direction (e.g. facing tissue) and be arranged in linear fashion. This arrangement results in more accurate temperature readings which, in turn, results in better temperature control. As such, the actual tissue temperature will more accurately correspond to the temperature set by the physician on the power supply and control device, thereby providing the physician with better control of the lesion creation process and reducing the likelihood that embolic materials will be formed. A reference thermocouple may also be provided.

The power supply and control system 200 includes an electrosurgical unit ("ESU") 202 that supplies and controls RF power. A suitable ESU is the Model 4810 ESU sold by Boston Scientific Corporation of Natick, Mass., which is capable of supplying and controlling power on an electrode-by-electrode basis. This is sometimes referred to as "multi-channel control." The ESU 202 transmits energy to the coagulation electrodes and receives signal from the temperature sensors by way of a cable 204 and a connector 206, which may be connected to the PC board on the surgical probe or clamp in the manner described above. The amount of power required to coagulate tissue ranges from 5 to 150 W. The exemplary ESU 202 is operable in a bipolar mode, where tissue coagulation energy emitted by one of the coagulation electrodes is returned through one of the other coagulation electrodes, and a unipolar mode, where the tissue coagulation energy emitted by the coagulation electrodes is returned through one or more indifferent electrodes 208 that are externally attached to the skin of the patient with a patch, or one or more electrodes (not shown) that are positioned in the blood pool, and a cable 210. Information concerning suitable temperature sensing and RF power supply and control is disclosed in U.S. Pat. Nos. 5,456,682, 5,582,609 and 5,755,715. Another alternative is to supply power in the combined bipolar/unipolar mode described in U.S. application Ser. No. 10/368,108, which is entitled "Power Supply And Control Apparatus And Electrophysiology Systems For Use With Same" and incorporated herein by reference.

With respect to the surgical systems 10, 11 and 20 illustrated in FIGS. 1-15, a single power line 126 is connected to each coagulation electrode 110. Typically, there are two temperature sensors 130 for each coagulation electrode 110. The ESU 202 individually powers and controls each coagulation electrode 110 based on the hottest of the two measured temperatures at that particular electrode.

In the surgical system 30 illustrated in FIGS. 16-24H, first and second power lines 536 are respectively connected to the longitudinal ends of the coagulation electrode 526a, first and second return lines 538 are respectively connected to the longitudinal ends of the coagulation electrode 526b, and two pairs of temperature sensors 130 (i.e. four temperature sensors) are provided for each of the coagulation electrodes. Each temperature sensor pair includes one temperature sensor 130 at a longitudinal end of the associated coagulation electrode and one temperature sensor located a distance equal to about ⅓ of the total electrode length from the longitudinal end. The ESU 202 will typically be operated in bipolar mode and energy supplied to the coagulation electrode 526a will be returned to the ESU by way of the coagulation electrode 526b. As such, the ESU connector 206' is connected to the power supply and return lines 536 and 538.

The ESU 202 in the exemplary surgical system 30 may be used to individually power and control two portions of the coagulation electrode 526a (one portion on either side of the longitudinal mid-point of the electrode) during a lesion formation procedure. Power to each portion, which has one power line 536 connected thereto and two temperature sensors 130 associated therewith, is controlled based on the highest of the two temperatures sensed by the two temperature sensors associated with that portion. Additional details concerning this power supply and control technique are provided in U.S. application Ser. No. 10/255,025, which is entitled "Electrophysiology Electrode Having Multiple Power Connections And Electrophysiology Devices Including The Same" and incorporated herein by reference.

The exemplary ESU 202 is also provided with power output and return connectors 212 and 214 (FIGS. 1, 6A, 7 and 16), for connection to corresponding connectors on the power output and return cables 204 and 210, that have different configurations in order to prevent improper connections.

VI. Stimulation Electrodes and Lesion Confirmation

In addition to forming lesions, the exemplary surgical systems illustrated in FIGS. 1-24H may also be used to determine whether or not therapeutic lesions have been properly formed by, for example, supplying tissue stimulation energy on one side of a lesion. The tissue on the other side of the lesion may then be monitored to determine whether an excitation block (typically the result of a continuous transmural lesion) has been formed in the target tissue. Tissue stimulation energy may also be used to determine lesion depth, which in turn, allows the physician to determine whether or not a lesion is transmural. In the exemplary implementations, the tissue stimulation energy is provided by a tissue stimulation apparatus 300 that is capable of providing a pulse of energy that stimulates (but does not coagulate) tissue. One exemplary tissue stimulation apparatus 300 is a conventional pacing apparatus, such as the Medtronic Model Nos. 5330 and 5388 external pulse generators. An ECG machine that is capable of monitoring and recording electrical impulses sensed by electrodes may also be provided.

With respect to the stimulation energy, the power delivered to tissue for stimulation purposes will typically be significantly less than that which would form a transmural or otherwise therapeutic lesion in tissue. With respect to the larger stimulation electrodes 112, 114, 528a, 528b, 529a1, 529a2, 529b1 and 529a2 discussed with respect to FIGS. 1-6B, 16-21 and 24A-24H, which may also be used for sensing, an exemplary stimulation energy delivery would consist of two stimulation pulses per second, each pulse being 1 millisecond. The maximum amplitude would be 20 mA, which would create 1 V, for a total power delivery of 40 μW. Turning to the smaller stimulation and sensing electrodes 426, 428 and 604, an exemplary stimulation energy delivery would consist of two stimulation pulses per second, each pulse being 1 millisecond. The maximum amplitude would be 10 mA, which would create 0.5 V, for a total power delivery of 10 μW. As noted above, the amount of power required to coagulate tissue ranges from 5 to 150 W.

In order to facilitate the connection to the tissue stimulation apparatus 300, the surgical devices discussed above with reference to FIGS. 1-6 and 16-32 are connectors 302 (both transmission and return) that are typically associated with pacing apparatus. Suitable connectors include, for example, 2 mm Hirshman pins. The connectors 302 may be individually connected to the tissue stimulation apparatus 300 (as shown) or combined into a single unit. The configuration of the connectors 302 will also typically be different than the ESU connectors 212 and 214 to prevent improper connections. In the embodiment illustrated in FIGS. 6A and 6B, on the other hand, there are far more stimulation electrodes and a single connector 117 is used to connect the stimulation electrodes to the EP recording apparatus 301. Similarly, in FIGS. 7-15, where there are many stimulation electrodes, as well as a corresponding number of sensing electrodes, a single connector 442 is used to connect the electrodes to the EP recording apparatus 301. A suitable EP recording apparatus is the Prucka CardioLab 7000® from GE Medical Systems. Preferably, the configuration of the connectors 117 and 442 will be different than the ESU connectors 212 and 214 to prevent improper connections.

It should also be noted that the functionality of the tissue stimulation apparatus 300 may be incorporated into the ESU 202. Here, however, ESU and associated surgical devices should be configured such that coagulation electrodes will only receive coagulation energy and the stimulation electrodes will only receive stimulation energy. Here too, this may be accomplished with different connector configurations. The functionality of the tissue stimulation apparatus 300 and the EP recording apparatus 301 may also be combined into a single device.

Generally speaking, the present surgical systems may be used to test the effectiveness of a lesion as follows. After the lesion is formed, the physician may use the same surgical device that was used to form the lesion (e.g. the surgical probe, surgical probe and suction device, or clamp based electrophysiology device) to perform a lesion evaluation. As discussed in greater detail below, the stimulation electrodes that are provided on surgical devices may be used to stimulate tissue on one side of a lesion by pacing at a higher rate than normal (e.g. 120 beats/minute). The local activation, if any, on the other side of the lesion will indicate whether or not the excitation block is incomplete. The stimulation electrodes may also be used to sense tissue within an isolated tissue region around which a lesion has been formed. Local activation within the isolated region from the heart's natural stimulation is indicative of a gap in the lesion. Additionally, the stimulation electrodes may be used to determine lesion depth.

There are a number of benefits associated with the present surgical systems. For example, the placement of tissue stimulation electrodes on the same surgical device as the tissue coagulation electrodes allows the physician to quickly and easily evaluate a lesion after it has been formed.

Referring to the exemplary surgical system 10 illustrated in FIGS. 1-6, the surgical probe 100 is provided with a pair of tissue stimulation electrodes 112 and 114 that may be connected to the tissue stimulation apparatus 300 and used to provide stimulation energy. The tissue stimulation electrodes 112 and 114 may also be used for sensing local tissue activation. Typically, the stimulation electrodes 112 and 114 will operate in a bipolar mode, but may be operated in unipolar mode if desired. The stimulation electrodes 112 and 114 are typically relatively small (i.e. too small to form transmural myocardial lesions). In the exemplary embodiment, stimulation electrode 112 is a ring electrode that is about 0.5 mm to 2 mm in length, the stimulation electrode 114 is a tip electrode that is about 0.5 mm to 2 mm in length, and the spacing therebetween is about 0.5 mm to 2 mm. Alternatively, the stimulation electrode 114 may be in the form of a ring electrode. Stimulation electrode 112 is about 1 mm to 3 mm from the distal-most coagulation electrode 110. With respect to materials, the stimulation electrodes 112 and 114 may be formed from the same materials as the coagulation electrodes 110. The diameter of the electrodes 112 and 114 preferably ranges from about 1.5 mm to about 3 mm for cardiovascular applications and, in one preferred implementation, the outer diameter is about 2 mm.

The exemplary surgical system 10 may be used to test the quality of lesions formed during a lesion formation procedure in a variety of ways. In the context of pulmonary vein isolation, for example, the coagulation electrodes 110 may be used to form continuous lesions around the pulmonary veins to isolated them from the left atria. Typically, a first lesion will be formed around the right pulmonary vein pair and a second lesion will be formed around the left pulmonary vein pair. The stimulation electrodes 112 and 114 may then be used to provide stimulation energy to the area within the first lesion. The tissue on the other side of the lesion may be monitored (electrically or visually) to determine whether the excitation block formed by the first lesion is complete. A similar procedure may be performed with respect to the second lesion. Alternatively, the stimulation electrodes 112 and 114 may be used to sense tissue within the area defined by the first lesion to determine whether heart's natural stimulation will produce local activation within the tissue area defined by the lesion. No local activation within the area defined by the lesion is indicative of the formation of a complete excitation block, while local activation is indicative of a gap in the lesion. A similar procedure may be performed with respect to the second lesion. It should also be noted that the surgical system 10 may be used both epicardial and endocardial procedures and that stimulation electrodes 112 and 114 may be used individually in unipolar versions of the aforementioned procedures if desired.

The tissue stimulation electrodes 112 and 114 in the exemplary surgical probe 101 illustrated in FIGS. 6A and 6B have the same configuration as the tissue stimulation electrodes in the surgical probe 100 and the surgical system 11 may be used to test the quality of lesions in the manner described above. Additionally, the surgical system 11 may be used to determine lesion depth and, correspondingly, whether or not a lesion is transmural at various points along the length of the lesion. Stimulation energy may be used to determine lesion depth because non-viable tissue (e.g. coagulated tissue) cannot be stimulated and will not propagate stimulation energy to nearby tissue. As such, when the application of stimulation energy that should stimulate tissue at a known depth fails to do so, and that depth is greater than or equal to the thickness of the body structure, it may be inferred that a transmural lesion has been formed.

In the context of lesions formed within the heart, for example, localized current densities must exceed about 2 mA/cm$^2$ to stimulate heart tissue. With respect to current transmitted from an electrode to tissue, the current density is about $1/2\pi r^2$, where r is the distance from the electrode. Thus, a 1 mA stimulation pulse will typically stimulate viable tissue that is no more than about 2.8 mm from the electrode, a 2 mA stimulation pulse will typically stimulate viable tissue that is no more than about 4.0 mm from the electrode, a 10 mA stimulation pulse will typically stimulate viable tissue that is no more than about 9.0 mm from the electrode, and a 20 mA stimulation pulse will typically stimulate viable tissue that is no more than about 13.0 mm from the electrode. By varying the amplitude of the stimulation energy pulses over a range of 1 to 20 mA, it is possible to determine how far viable tissue is from the electrode. For example, the left atrium is about 3 mm thick and accordingly, failure to stimulate with a 2 mA stimulation pulse indicates that a transmural lesion has been formed in the vicinity of the stimulation electrode.

Referring to the exemplary surgical probe 101, and as noted above, the tissue stimulation electrodes 112 are located between the coagulation electrodes 110 and proximal of the proximal-most coagulation electrode, while the stimulation electrode 114 is distal of the distal-most coagulation electrode. This arrangement allows the physician to test various points along the length of a lesion when all of the coagulation electrodes 110 are used to form the lesion (without moving the probe). Alternatively, if only the middle three coagulation electrodes 110 are used to form a lesion, for example, then the adjacent four tissue stimulation electrodes 112 could be used to stimulate tissue to determine whether or not the lesion is transmural.

The exemplary surgical system 11 may be used to test the quality of lesions formed during a lesion formation procedure in a variety of ways. In the context of lesions within the left atrium, for example, the coagulation electrodes 110 may be used to form a continuous lesion (e.g. around one or more pulmonary veins, or as part of a pattern of therapeutic lesions). After the lesion has been formed, and without moving the surgical probe 101, one or more of the stimulation electrodes 112 and 114 may be used to provide stimulation energy to the coagulated tissue. For example, the stimulation electrodes 112 and 114, which are located along the linear or curvilinear region of coagulated tissue may be individually provided with pulses of stimulation energy. The magnitude of the pulses, which should be chosen so as to correspond to the thickness of the tissue structure, will be about 2 mA in the left atrium example. Viable tissue within the left atrium may be monitored (electrically or visually) after each pulse to determine whether the lesion is transmural. More specifically, a lack of local activation within the left atrium from the pulse indicates that the lesion is deep enough (i.e. transmural) in the vicinity of the associated stimulation electrode, while local activation indicates that the lesion is not transmural in the region of the stimulation electrode. In those instances where the lesion (or portion thereof) is not transmural, additional coagulation with the coagulation electrodes 110, typically at a higher power level than originally employed, may be performed. It should also be noted that the surgical system 11 may be used both epicardial and endocardial procedures.

Turning to the exemplary surgical system 20 illustrated in FIGS. 7-15, and referring more specifically to FIG. 14, the suction device 404 is provided with longitudinally extending bipolar pairs of tissue stimulation electrodes 426 and longitudinally extending bipolar pairs of sensing electrodes 428 near the lateral edges of the suction device. In the illustrated embodiment, a plurality of bipolar pairs of stimulation electrodes 426 extend along essentially the entire length of one side of the suction device 404, while a plurality of bipolar pairs of sensing electrodes 428 extend along essentially the entire length of the other side of the suction device. Each bipolar pair is adjacent to one of the suction ports 410 and, accordingly, the electrodes will be held firmly against tissue when suction force is applied. The stimulation electrodes 426 are located on one side of the slot 420 and the sensing electrodes 428 are located on the other. As such, the tissue stimulation and sensing electrodes 426 and 428 will be on opposite sides of the surgical probe distal section 108 and the coagulation electrodes 110, as well as on opposite sides of the lesion formed by the coagulation electrodes.

There are, of course, a wide variety of alternative stimulation and sensing electrode schemes. By way of example, but not limitation, the number of bipolar pairs of tissue stimulation and sensing electrodes 426 and 428 may range from a large number of pairs (as shown) to a single pair tissue stimulation electrodes and a single pair sensing electrodes. The single pairs may be located near the middle (measured longitudinally) of the suction device 404. Another alternative is unipolar stimulation and sensing. Here, single stimulation electrodes (as opposed to a bipolar pair) may be positioned adjacent to each of the suction ports 410 on one side of the suction device 404 and single sensing electrodes may be positioned adjacent to each of the suction ports on the other side of the suction device.

With respect to configuration and manufacture, the exemplary tissue stimulation and sensing electrodes 426 and 428 may be relatively small (i.e. too small to form transmural myocardial lesions), low profile devices. Suitable sizes are about 0.5 mm to 1 mm in diameter, and a suitable thickness is about 0.01 mm. Such electrodes may be formed by coating a conductive material onto the suction device 404 using conventional coating techniques or an IBAD process. Suitable conductive materials include platinum-iridium and gold. An undercoating of nickel, silver or titanium may be applied to improve adherence. Conductive ink compounds, such as silver-based flexible adhesive conductive ink (polyurethane binder) or metal-based adhesive conductive inks (e.g. platinum, gold, or copper based) may also be pad printed onto the suction device 404. The signal lines 430 and 434 are also very thin (e.g. about 40-50 gauge wires).

The exemplary surgical system 20 may be used to test the quality of lesions formed during a lesion formation procedure in a variety of ways. For example, the suction source 402 may be used to maintain the position of the suction device 404 after power transmission from the coagulation electrodes 110 on surgical probe 100' has ended. A pulse of stimulation energy (here, about 10 mA) may be applied to viable tissue on one side of the lesion by a pair of stimulation electrodes (such as the pair identified by reference numeral 426a in FIG. 14). The viable tissue on the other side of the lesion may be monitored with a pair of sensing electrodes (such as the pair identified by reference numeral 428a in FIG. 14) to detect the local excitation from the pulse of stimulation energy. The tissue stimulation apparatus 300 will measure the amount of time between the delivery of the pulse to the tissue by the stimulation electrode pair 426a and the detection of the local activation by the sensing electrode pair 428a on the other side of the lesion. The amount of time that between pulse delivery on one side of the lesion and local activation on the other (sometimes referred to as a "conduction delay") is indicative of the quality of the lesion.

In the context of the formation of lesions within the heart, the conduction delay from the stimulation electrode pair 426a and the sensing electrode pair 428a will typically be about 10 ms when the distance between the pairs is about 1 cm, absent a conduction block. Here, the excitation pulse will travel a relatively short distance. Conversely, when a complete conduction block is formed between the stimulation and sensing pairs, the excitation pulse will be forced to travel around the lesion. The longer travel distance results in a longer conduction delay, which is indicative of the formation of a therapeutic lesion. For example, a continuous 50 cm transmural lesion that creates a complete conduction block along its length will typical increase the conduction delay to about 50 ms.

The exemplary EP recording apparatus 301 may be configured to simply display measured conduction delays. Alternatively, the EP recording apparatus 301 may be used to store expected propagation delays for various tissue types and suction device configurations (including the positioning of the stimulation and sensing electrodes). The EP recording apparatus 301 will compare the expected propagation delay (e.g. 10 ms) with no block to the measured propagation delay (e.g. 50 ms) and determine whether or not a complete conduction block has been formed. The EP recording apparatus 301 would then provide an audible or visual indication concerning the status of the lesion.

It should also be noted that, in a preferred testing method, the lesion will be tested at various points along its length, one point at a time. The lesion may be tested with each of the stimulation and sensing electrode pairs that are adjacent to a coagulation electrode that was used to form a lesion. If for example, the proximal four coagulation electrodes are used to form a lesion, then the proximal four pairs of stimulation and sensing electrodes will be used (one stimulation/sensing at a time) to determine whether or not the lesion creating procedure created a complete conduction block.

Referring now to the exemplary surgical system 30 illustrated in FIGS. 16-24B, and to FIG. 16 in particular, the energy transmission and stimulation assembly 524 includes first and second tissue stimulation electrodes 528a and 528b. The stimulation electrodes 528a and 528b are preferably tip electrodes that are about 1 mm to 2 mm in length, about 2 mm to 4 mm in diameter, and carried on the distal ends of the support structures 530a and 530b. The stimulation electrodes 528a and 528b are also about 1 mm to 3 mm from the distal ends of the coagulation electrodes 526a and 526b. The stimulation electrodes may, alternatively, be ring electrodes that are carried near the distal ends of the support structures 530a and 530b. Another alternative is to place both stimulation electrodes on one of the support structures in a manner similar to the surgical probe 100 illustrated in FIG. 1. The stimulation electrodes 528a and 528b may also be formed from the materials and methods described above with respect to stimulation electrodes 112 and 114.

Turning to exemplary energy transmission and stimulation assembly 524' illustrated in FIGS. 24C-24H, the stimulation electrodes 529a1/529a2 and 529b1/529b2 are typically relatively small ring electrodes (i.e. too small to form transmural myocardial lesions) that are about 0.5 mm to 2 mm in length and about 1.5 mm to 3 mm in diameter.

The exemplary surgical system 30 may be used to test the quality of lesions formed during a lesion formation procedure in a variety of ways. For example, in the context of the treatment of atrial fibrillation, the surgical system 30 may be used to form lesions around one or more pulmonary veins to isolated the left atria from arrhythmias that originate in the pulmonary veins. In one exemplary procedure, the clamp 502 may be positioned around a pair of pulmonary veins and the coagulation electrodes 526a and 526b used to form a lesion around the pair. The stimulation electrodes 528a and 528b may then be used to supply a bipolar pacing pulse (e.g. about 20 mA) on the side of the lesion opposite the left atrium. The physician can determine whether or not a therapeutic lesion (or "complete block") has been formed by observing the left atrium. If the pacing pulse is able to cross the lesion, the heart will beat faster (e.g. 120 beats/minute). This may be determined by observation or by use of an ECG machine that is monitoring the heart. Here, additional coagulation will be required to complete the lesion. The failure to stimulate the heart from the side of the lesion opposite the left atrium is, on the other hand, indicative of the formation of a therapeutic lesion. Nevertheless, because muscle bundles are not always connected near the pulmonary veins, it is preferable that the stimulation energy be applied to a number of tissue areas on the side of the lesion opposite the left atrium to reduce the possibility of false negatives.

Alternatively, the stimulation electrodes 528a and 528b may then be used to monitor tissue within the region that was intended to be isolated. In the context of pulmonary vein isolation, for example, the stimulation electrodes 528a and 528b may be placed in contact with viable tissue on the pulmonary vein side of the lesion. Local activation within the isolated region from the heart's natural stimulation is indicative of a gap in the lesion.

The stimulation electrodes 528a and 528b may also be used in a unipolar operation similar to the bipolar operation discussed above with reference to stimulation and sensing electrodes pairs 426a and 428a. More specifically, the clamp members 514 and 516 may be positioned such that the electrodes 528a and 528b are on opposite sides of a continuous linear or curvilinear lesion. For example, electrode 528a may be placed within the left atrium and electrode 528b may be placed on the pulmonary vein side of a pulmonary vein ostium. A pulse of stimulation energy (about 10 mA) may be applied to viable tissue on one side of the lesion by the electrode 528a and the viable tissue on the other side of the lesion may be monitored with the electrode 528b to detect whether or not there is local excitation from the pulse of stimulation energy.

Additionally, the surgical system 30 may be used to determine whether or not a lesion is transmural. Here, the electrodes 528a and 528b may be placed on opposite surfaces of the lesion (e.g. the epicardial and endocardial surfaces, or two epicardial surfaces).

Turning to FIGS. 24C-24H, in those instances in which the exemplary surgical system 30 includes the exemplary energy transmission and stimulation assembly 524', the stimulation electrodes 529a1/529a2 and 529b1/529b2 may be used to test a lesion formed with the coagulation electrodes 526a and 526b without moving the clamp 502. For example, after the lesion is formed, a pulse of stimulation energy (here, about 10 mA) may be applied to viable tissue on one side of the lesion by stimulation electrodes 529a1/529a2, while viable tissue on the other side of the lesion may be monitored with stimulation electrodes 529b1/529b2 to detect the local excitation from the pulse of stimulation energy. The tissue stimulation apparatus 300 will measure the conduction delay between the delivery of the pulse to the tissue on one side of the lesion and the detection of the local activation on the other side of the lesion. The conduction delay is, as noted above, indicative of the quality of the lesion.

VII. Tissue Stimulation and Sensing Probes

As illustrated for example in FIGS. 25-28, a surgical tissue stimulation and sensing system 40 in accordance with one embodiment of a present invention includes a tissue stimulation apparatus 300 and a tissue stimulation and sensing probe 600. The tissue stimulation apparatus 300 is described above. The exemplary tissue stimulation and sensing probe 600 includes a tissue engagement device 602 that carries a pair of stimulation electrodes 604 and is supported on the distal end of a shaft 606. The electrodes 604 may be used to sense electrical actively in addition to transmitting stimulation energy.

The specific size and shape of the tissue engagement device 602 will, of course, depend on the intended application, as will the choice of materials. Although the present inventions are not limited to any particular sizes, shapes or materials, one exemplary implementation that is especially well suited for cardiac treatment is described hereafter. The exemplary tissue engagement device 602 cup-shaped and is formed, preferably by molding, from a soft, flexible biocompatible material such as silicone rubber or urethane. The diameter of the tissue engagement device 602 may range from about 2 mm to about 5 mm and is about 2-3 mm in the exemplary embodiment. With respect to the electrical connection of the stimulation electrodes 604 to the tissue stimulation apparatus 300, the stimulation electrodes in the exemplary implementation are connected to signal lines 608 that extend from the stimulation electrodes, though a shaft lumen 610, and an opening (not shown) at the proximal end of the shaft 606. The signal lines are connected to the connectors 302 on the stimulation apparatus 300 in the manner discussed above.

In the exemplary implementations illustrated in FIGS. 25-32, the stimulation electrodes 604 are essentially the same as the stimulation and sensing electrodes 426 and 428 described above. For example, the electrodes 604 may be relatively small, low profile devices (e.g. about 0.5 mm to 1 mm in diameter and about 0.01 mm thick) that can be formed by coating one of the suitable conductive materials described above onto the tissue engagement device 602.

Turning to the particulars of the exemplary shaft 606, the shaft in the illustrated embodiment is relatively short and relatively stiff. More specifically, the exemplary shaft 606 is about 20 cm to 50 cm in length and is formed from a malleable hypotube 612 with an outer tubing 614 formed from Pebax® material, polyurethane, or other suitable materials. A typical hypotube would be about 2 mm and 8 mm in diameter. The stiffness of the shaft 606 allows the physician to firmly place the electrodes 604 against tissue, while the malleability of the shaft allows the physician to vary the shape of the shaft as desired to suit particular needs.

The exemplary surgical tissue stimulation and sensing system 40 may be used to, for example, test the quality of lesions formed during a lesion formation procedure in a variety of ways. For example, the physician may first bend the shaft 606 into the appropriate shape to reach to the target tissue. The shaft 606 may, of course, also be used in a linear orientation. The tissue engagement device 602 may be placed against tissue on one side of a lesion and the stimulation electrodes 604 may be used to apply stimulation energy to the tissue. For example, the tissue engagement device 602 may be placed on the pulmonary vein side of a pulmonary vein isolation lesion. The stimulation energy may be in the form of a bipolar pacing pulse (e.g. 10 mA). The physician can determine whether or not a therapeutic lesion (or "complete block") has been formed by observing the tissue on the other side of the lesion. If the pacing pulse is able to cross the lesion, the heart will beat faster (e.g. 120 beats/minute). This may be determined by observation or by use of an ECG machine that is monitoring the heart.

Alternatively, the stimulation electrodes 604 may be used to sense tissue within the area defined by a lesion to determine whether heart's natural stimulation will produce local activation within the tissue area defined by the lesion. For example, the tissue engagement device 602 may be placed on the pulmonary vein side of a pulmonary vein isolation lesion. No local activation within the area defined by the lesion is indicative of the formation of a complete excitation block, while local activation is indicative of a gap in the lesion.

Other methods involve the use of two or more of the tissue stimulation and sensing probes 600. For example, the tissue engagement devices 602 of two separate probes may be placed against tissue on opposite sides of a lesion. The stimulation electrodes 604 of one probe may be used to apply stimulation energy to the tissue, while the stimulation electrodes on the other may be used to sense local activation. This technique may be used to, amongst other things, test lesions that are formed around one or more of the pulmonary veins. Here, the stimulation electrodes 604 of one probe may be placed against tissue within the left atrium and stimulation electrodes 604 of another probe may be placed on the pulmonary vein side of a pulmonary vein ostium. A pulse of stimulation energy (about 10 mA) may be applied to viable tissue on one side of the lesion and the viable tissue on the other side of the lesion may be monitored to detect the local excitation from the pulse of stimulation energy.

Figure 27A:
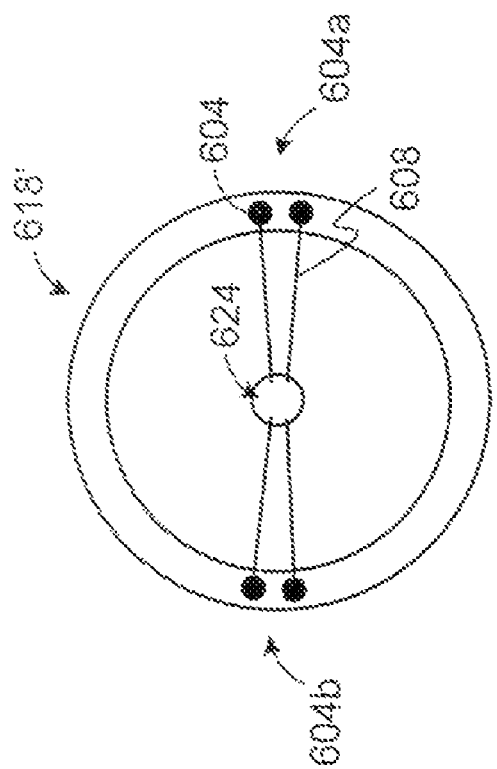
FIG. 27A is an end view of a probe in accordance with one embodiment of a present invention.

Turning to FIG. 27A, in an alternative implementation, a tissue engagement device 602' that is substantially larger than the tissue engagement device 602 (e.g. about 1 cm in diameter) may be provided on the end of the shaft 606. The tissue engagement device 602' supports two pairs of stimulation electrodes 604 (i.e. pairs 604a and 604b). Each pair may be operated in bipolar fashion in a manner similar to that described above with reference to electrode pairs 426a and 428a. For example, the pairs of stimulation electrodes may the positioned on opposite sides of a continuous linear or curvilinear lesion. A pulse of stimulation energy (about 10 mA) may be applied to viable tissue on one side of the lesion by the electrodes in pair 604a and the viable tissue on the other side of the lesion may be monitored with the electrodes in pair 604b to detect the local excitation from the pulse of stimulation energy. As noted above, the conduction delay will be indicative of the quality of the lesion.

There are a number of advantages associated with the exemplary tissue stimulation and sensing probe 600. For example, using the tissue stimulation and sensing probe 600 to place stimulation electrodes against tissue is much easier than the conventional method of securing pacing electrodes to tissue, which involves suturing the pacing electrodes to tissue, especially in those instances where the stimulation electrodes will only be in place for a short time. The stimulation and sensing probe 600 also makes it much easier to remove the stimulation electrodes 604 from the patient, or move the electrodes to a new tissue location, as compared to pacing electrodes that are sutured to tissue. It should also be noted the stimulation and sensing probe 600 may be used in a pacing procedure, especially one in which it is desirable to pace at numerous locations within the heart.

Figure 29:
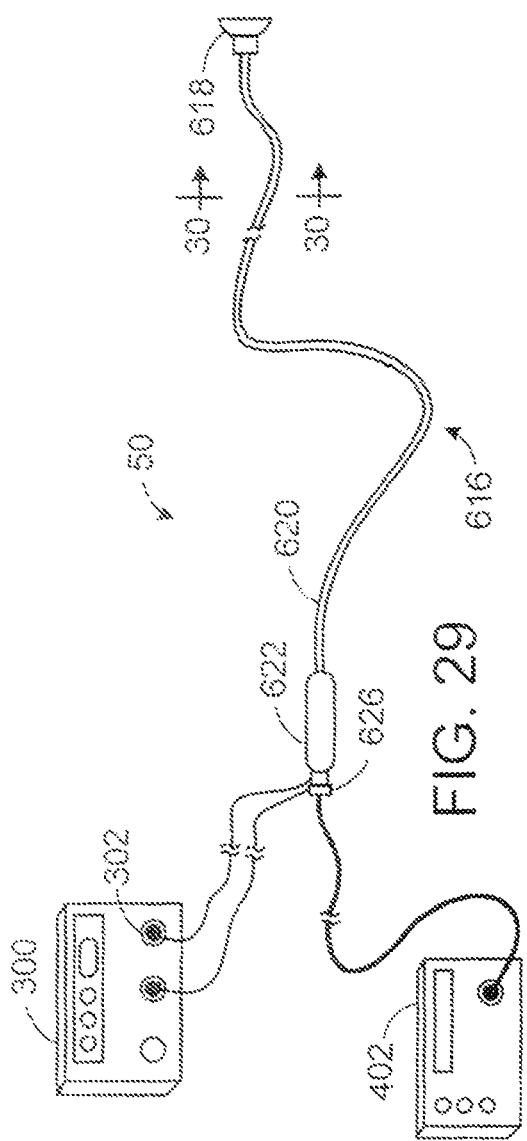
FIG. 29 is a perspective view of a surgical system in accordance with a preferred embodiment of a present invention.
Figure 31:
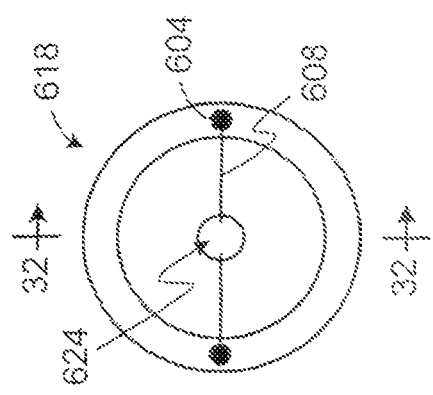
FIG. 31 is an end view of a probe in accordance with one embodiment of a present invention.
Figure 30:
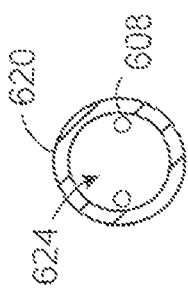
FIG. 30 is a section view taken along line 30-30 in FIG. 29.

Another surgical tissue stimulation and sensing system, which is generally represented by reference numeral 50 in FIG. 29 includes a tissue stimulation apparatus 300, a suction source 402 and a tissue stimulation and sensing probe 616. The tissue stimulation apparatus 300 and a suction source 402 are described above. The exemplary tissue stimulation and sensing probe 616 includes a suction device 618 that carries a pair of stimulation electrodes 604 and is supported on the distal end of a flexible tube 620. The proximal end of the flexible tube 620 is connected to a handle 622. The suction device 616 is connected to the suction source 402 by way of a lumen 624 that extends through the flexible tube 620 and a flexible tube 406 that is connected to the proximal end of the handle 622 by a connector 626 such as, for example, the illustrated Luer connector. When the suction source 402 is actuated, the suction device 602 will fix the stimulation electrodes 604 against the target tissue.

The specific size and shape of the suction device 618 will, of course, depend on the intended application, as will the choice of materials. Although the present inventions are not limited to any particular sizes, shapes or materials, one exemplary implementation that is especially well suited for cardiac treatment is described hereafter. The suction device 618 is formed, preferably by molding, from a soft, flexible biocompatible material such as silicone rubber or urethane. The diameter of the suction device 618 may range from about 2 mm to about 10 mm and is about 2-3 mm in the exemplary embodiment. With respect to the connection of the stimulation electrodes to the 604 to the tissue stimulation apparatus 300, signal lines 612 extend from the stimulation electrodes though the lumen 624 and though a pair of openings (not shown) in the handle 622. The flexible tube 620, which may be formed from polyurethane, Santoprene® or other suitable materials, is preferably about 20 cm to about 100 cm in length.

The exemplary surgical tissue stimulation and sensing system 50 may be used to, for example, test the quality of lesions formed during a lesion formation procedure in a variety of ways. For example, the suction device 618 may be secured to tissue on one side of a lesion, either before or after the lesion is formed. This may be accomplished by placing the suction device 618 against tissue (typically with a forceps or other suitable surgical instrument) and then actuating the suction source 402. The stimulation electrodes 604 may then be used to apply stimulation energy to the tissue. The stimulation energy may be in the form of a bipolar pacing pulse (e.g. 10 mA). The physician can determine whether or not a therapeutic lesion (or "complete block") has been formed by observing the tissue on the other side of the lesion. If the pacing pulse is able to cross the lesion, the heart will beat faster (e.g. 120 beats/minute). This may be determined by observation or by use of an ECG machine that is monitoring the heart. Alternatively, the stimulation electrodes may be used to sense tissue within an isolated region in the manner described above in order to determine whether a complete line of block has been formed.

Other methods involve the use of two or more of the tissue stimulation and sensing probes 616. For example, the suction device 618 of two separate probes may be placed against tissue on opposite sides of a lesion. The stimulation electrodes 604 of one probe may be used to apply stimulation energy to the tissue, while the stimulation electrodes on the other may be used to sense local activation. This technique may be used to, amongst other things, test lesions that are formed around one or more of the pulmonary veins. Here, the stimulation electrodes 604 of one probe may be placed against tissue within the left atrium and stimulation electrodes 604 of another probe may be placed on the pulmonary vein side of a pulmonary vein ostium. A pulse of stimulation energy (about 10 mA) may be applied to viable tissue on one side of the lesion and the viable tissue on the other side of the lesion may be monitored to detect the local excitation from the pulse of stimulation energy.

Figure 31A:
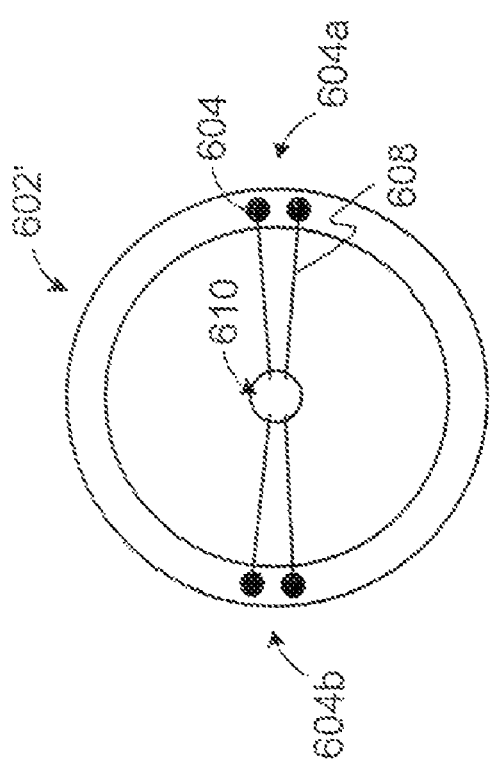
FIG. 31A is an end view of a probe in accordance with one embodiment of a present invention.
Figure 32:
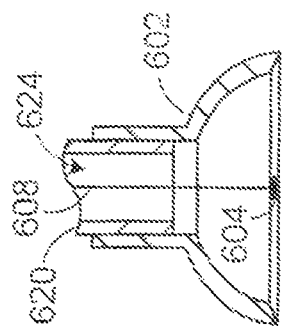
FIG. 32 is a section view taken along line 32-32 in FIG. 31.

Turning to FIG. 31A, in an alternative implementation, a suction device 618' that is substantially larger than the suction device 618 (e.g. about 1 cm in diameter) may be provided on the end of the tube 620. The suction device 618' supports two pairs of stimulation electrodes 604 (i.e. pairs 604a and 604b). Each pair may be operated in bipolar fashion in a manner similar to that described above with reference FIG. 27A.

There are a number of advantages associated with the exemplary tissue stimulation probe 616. For example, using suction force to hold the stimulation electrodes 604 in place on the target tissue is much easier than the conventional method of securing pacing electrodes to tissue, i.e. suturing the pacing electrodes to tissue. The stimulation probe 616 also makes it relatively easy to disconnect the electrodes 604 from the tissue, i.e. by simply ending the suction force, so that the electrodes may be removed from the patient or moved to a new location. The stimulation and sensing probe 616 may also be used in a pacing procedure, especially one in which it is desirable to pace at numerous locations within the heart.

Finally, it should be noted that a single stimulation electrode may be provided on the sensing probes 600 and 616, and a single stimulation electrode may be provided in place of each of the electrode pairs illustrated in FIGS. 27A and 31A.

VIII. Self-Anchoring Tissue Stimulation and Sensing Devices

As illustrated for example in FIGS. 33-36, a surgical tissue stimulation and sensing system 60 in accordance with one embodiment of a present invention includes a tissue stimulation apparatus 300 and a self-anchoring stimulation and sensing device 700. The tissue stimulation apparatus 300 is described above. The exemplary self-anchoring stimulation and sensing device 700 includes a pair of stimulation electrodes 702 that are supported on an anchor 704. The electrodes 702 may be used to sense electrical actively in addition to transmitting stimulation energy.

A wide variety of anchors may be employed. The exemplary anchor 704 illustrated in FIGS. 33-36 includes a flexible, pre-shaped carrier 706 and a pair of tissue piercing members 708. The exemplary carrier 706 has a pair of end portions 706a/706b and an interior portion 706c. When in an unstressed (or relaxed) state, the interior portion 706c will be in spaced relation to a surface, such as a tissue surface, which the end portions 706a/706b are in contact with. The carrier 706 and tissue piercing members 708 are dimensioned and positioned relative to one another such that the carrier will be deflected (and stressed) when the piercing members are placed into tissue. As a result, the stimulation electrodes 702 will be forced (or "biased") against the tissue when the piercing members 708 engage the tissue. The exemplary anchor 704 will be bent into a configuration that is flat, such that the interior portion 706c engages the tissue, or is close to flat, when the piercing members 708 are completely into the tissue.

The exemplary carrier 706 in the illustrated embodiment includes a flexible, pre-shaped spring member 710, which may be rectangular (as shown), circular or any other suitable shape in cross-section, and a soft plastic coating 712. Alternatively, a pre-shaped rubber (such as silicone rubber) carrier may be employed. The carrier 706 will typically be about 1 mm to 4 mm wide and about 6 mm to 20 mm long when flattened. The tissue piercing members 708 are malleable structures that are secured to the carrier 706 with a base 709. With respect to use, the tissue piercing members 708 are held with a clamp during the application and removal process. More specifically, a physician may use a clamp (such as the type of clamp used to attach surgical staples) to spread the piercing members 708 apart slightly, force the sharpened ends 714 into tissue until the carrier 706 is flat or close to flat, and then urge the piercing member towards one another to secure the self-anchoring stimulation and sensing device 700 to the tissue. The device 700 may be removed by simply spreading the piercing members 708 apart slightly with a clamp (such as the type of clamp used to remove surgical staples) and pulling the device away from the tissue.

The exemplary stimulation electrodes 702 may be ring electrodes that are about 0.5 mm to 2 mm in length and are otherwise similar to the ring-shaped stimulation electrodes described above. Alternatively, the stimulation electrodes may be relatively small, low profile devices (e.g. about 0.5 mm to 1 mm in diameter, and about 0.01 mm thick) located on the tissue facing side of the carrier 706. Such electrodes may be formed by coating a conductive material onto the carrier 706 using conventional coating techniques or an IBAD process.

The electrodes are connected by signal lines 716 that extend from the stimulation electrodes 702 and along portions of the carrier 706. The signal lines 716 are connected to the connectors 302 on the stimulation apparatus 300 in the manner discussed above. An overcoat 718 may also be provided.

Another exemplary self-anchoring stimulation and sensing device is generally represented by reference numeral 720 in FIGS. 37 and 38. The device illustrated in FIGS. 37 and 38 is substantially similar to the device illustrated in FIGS. 33-36 and similar elements are represented by similar reference numerals. Here, however, the exemplary anchor 722 includes the flexible, pre-shaped carrier 706 and a rotatable tissue piercing device 724 that is associated with the interior portion 706c. The rotatable tissue piercing device 724 has a helical member 726 that is connected to a knob 728. Rotation of the knob 728 in one direction will cause the helical member 726 to screw into the tissue. The rotation may continue until the carrier 706 is flat or close to flat, the interior portion 706c is against tissue or close to the tissue, and the stimulation electrodes 702 are forced against the tissue by the carrier. Rotation of the knob 728 in the other direction will unscrew the helical member 726 and facilitate removal of the stimulation and sensing device 720.

Still another exemplary self-anchoring stimulation and sensing device is generally represented by reference numeral 730 in FIGS. 39 and 40. The device illustrated in FIGS. 39 and 40 is substantially similar to the devices illustrated in FIGS. 33-38 and similar elements are represented by similar reference numerals. Here, however, the exemplary anchor 732 does not pierce the tissue. The anchor 732 is, instead, secured to the tissue with a layer of adhesive 734 on the carrier interior portion 706c. Suitable adhesives include cyanoacrylate and thrombin adhesive. A release layer 736 may also be provided. During use, the physician can remove the release layer 736, place the stimulation and sensing device 730 onto the tissue, and press the interior portion 706c down until the adhesive 734 contacts tissue, thereby securing the interior portion to the tissue and forcing the electrodes 702 into close contact with the tissue. The physician will simply peel the stimulation and sensing device 730 off when the procedure is complete.

The exemplary surgical tissue stimulation and sensing system 60 may be used to, for example, test the quality of lesions formed during a lesion formation procedure in a variety of ways. For example, one or more of the stimulation and sensing devices 700, 720 and 730 may be secured to tissue on one side of a lesion, either before or after the lesion is formed. The stimulation electrodes 702 may then be used to apply stimulation energy to the tissue. The stimulation energy may be in the form of a bipolar pacing pulse (e.g. 10 mA). The physician can determine whether or not a therapeutic lesion (or "complete block") has 0.25 been formed by observing the tissue on the other side of the lesion. If the pacing pulse is able to cross the lesion, the heart will beat faster (e.g. 120 beats/minute). This may be determined by observation or by use of an ECG machine that is monitoring the heart. Alternatively, the stimulation electrodes may be used to sense tissue within an isolated region in the manner described above in order to determine whether a complete line of block has been formed.

Other methods involve the use of two or more of the stimulation and sensing devices 700, 720 and 730. For example, two separate stimulation and sensing devices 700, 720 or 730 may be placed against tissue on opposite sides of a lesion. The stimulation electrodes 702 on one may be used to apply stimulation energy to the tissue, while the stimulation electrodes on the other may be used to sense local activation. As noted above, depending on the type of lesion being tested, the presence or absence of local activation or the conduction delay will be indicative of the quality of the lesion.

Although the present inventions have been described in terms of the preferred embodiments above, numerous modifications and/or additions to the above-described preferred embodiments would be readily apparent to one skilled in the art. By way of example, but not limitation, each of the devices described above may be used to pace prior to lesion formation and each of the methods described above may include pacing prior to lesion formation. It is intended that the scope of the present inventions extend to all such modifications and/or additions and that the scope of the present inventions is limited solely by the claims set forth below.

What is claimed is:

1. A surgical apparatus, comprising:
a clamp including a first clamp member, a second clamp member, and movement apparatus that moves at least one of the first and second clamp members relative to the other of the first and second clamp members such that the surgical apparatus is operable between a first state defined by a first spacing between the first and second clamp members and a second state defined by a second spacing between the first and second clamp members, the first spacing being different from the second spacing;
an electrosurgical power supply and control apparatus;
a tissue stimulation apparatus configured to provide pulses of tissue stimulation energy varying in amplitude over a range of 1 mA to 20 mA;
a coagulation electrode assembly carried by the clamp, and coupleable with the electrosurgical power supply and control apparatus; and
a stimulation electrode assembly carried by the clamp, and coupleable with the tissue stimulation apparatus.

2. The surgical apparatus of claim 1, wherein each of the first and second clamp members have a pre-shaped curvature.

3. The surgical apparatus of claim 1, further comprising a locking device that locks the clamp so as to provide a spacing between the first and second clamp members.

4. The surgical apparatus of claim 1, wherein the coagulation electrode assembly comprises a first coagulation electrode coupled with the first clamp member and a second coagulation electrode coupled with the second clamp member.

5. The surgical apparatus of claim 1, wherein the stimulation electrode assembly comprises a first stimulation electrode coupled with the first clamp member and a second stimulation electrode coupled with the second clamp member.

6. The surgical apparatus of claim 5, wherein the source of stimulation energy is switchable between a bipolar mode and a unipolar mode, such that when in the bipolar mode the source of stimulation energy is operable to transmit stimulation energy to the first stimulation electrode and receive stimulation energy from the second stimulation electrode, and when in the unipolar mode the source of stimulation energy is operable to transmit stimulation energy to both the first stimulation electrode and the second stimulation electrode.

7. The surgical apparatus of claim 1, wherein the coagulation electrode assembly comprises a flexible coagulation electrode.

8. A surgical apparatus, comprising:
a clamp including a first clamp member, a second clamp member, and movement apparatus that moves at least one of the first and second clamp members relative to the other of the first and second clamp members such that the surgical apparatus is operable between a first state defined by a first spacing between the first and second clamp members and a second state defined by a second spacing between the first and second clamp members, the first spacing being different from the second spacing;
a coagulation electrode assembly carried by the clamp;
an electrosurgical power supply and control apparatus coupleable with the coagulation electrode assembly;
a stimulation electrode assembly carried by the clamp and comprising a first stimulation electrode; and
a tissue stimulation apparatus coupleable with the stimulation electrode assembly, and configured to provide pulses of tissue stimulation energy varying over a range between a first amplitude and a second amplitude,
wherein the first amplitude is sufficient to stimulate viable heart tissue that is no more than about 2.8 mm from the stimulation electrode when in contact with the heart tissue, and wherein the second amplitude is sufficient to stimulate viable heart tissue that is no more than about 13.0 mm from the stimulation electrode when contacting the heart tissue.

9. The surgical apparatus of claim 8, wherein each of the first and second clamp members have a pre-shaped curvature.

10. The surgical apparatus of claim 8, further comprising a locking device that locks the clamp so as to provide a spacing between the first and second clamp members.

11. The surgical apparatus of claim 8, wherein the coagulation electrode assembly comprises a first coagulation electrode coupled with the first clamp member and a second coagulation electrode coupled with the second clamp member.

12. The surgical apparatus of claim 8, wherein the stimulation electrode assembly further comprises a second stimulation electrode, the first stimulation electrode coupled with the first clamp member and the second stimulation electrode coupled with the second clamp member.

13. The surgical apparatus of claim 12, wherein the source of stimulation energy is switchable between a bipolar mode and a unipolar mode, such that when in the bipolar mode the source of stimulation energy is operable to transmit stimulation energy to the first stimulation electrode and receive stimulation energy from the second stimulation electrode, and when in the unipolar mode the source of stimulation energy is operable to transmit stimulation energy to both the first stimulation electrode and the second stimulation electrode.

14. The surgical apparatus of claim 8, wherein the coagulation electrode assembly comprises a flexible coagulation electrode.

* * * * *